(12) United States Patent
Anderson et al.

(10) Patent No.: US 9,970,002 B2
(45) Date of Patent: May 15, 2018

(54) COMPOSITIONS AND METHODS FOR FUNCTIONAL NUCLEIC ACID DELIVERY

(71) Applicants: Massachusetts Institute of Technology, Cambridge, MA (US); The Children's Medical Center Corporation, Boston, MA (US)

(72) Inventors: Daniel G. Anderson, Sudbury, MA (US); Rosemary Lynn Kanasty, Cambridge, MA (US); Arturo Jose Vegas, Cambridge, MA (US); Robert S. Langer, Newton, MA (US)

(73) Assignees: Massachusetts Institute of Technology, Cambridge, MA (US); The Children's Medical Center Corporation, Boston, MA (US)

( * ) Notice: Subject to any disclaimer, the term of this patent is extended or adjusted under 35 U.S.C. 154(b) by 1 day.

(21) Appl. No.: 14/652,038

(22) PCT Filed: Dec. 12, 2013

(86) PCT No.: PCT/US2013/074784
§ 371 (c)(1),
(2) Date: Jun. 12, 2015

(87) PCT Pub. No.: WO2014/093688
PCT Pub. Date: Jun. 19, 2014

(65) Prior Publication Data
US 2015/0322432 A1 Nov. 12, 2015

Related U.S. Application Data

(60) Provisional application No. 61/736,079, filed on Dec. 12, 2012.

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/14* (2013.01); *C12N 2310/351* (2013.01); *C12N 2310/3515* (2013.01); *C12N 2310/3517* (2013.01); *C12N 2320/32* (2013.01)

(58) Field of Classification Search
CPC . C12N 15/111; C12N 15/113; C12N 2310/14; C12N 2310/351; C12N 2310/3515; C12N 2310/3517; C12N 2320/32
USPC ........................................ 514/44 A; 536/24.5
See application file for complete search history.

(56) References Cited

U.S. PATENT DOCUMENTS

| 5,135,917 | A | 8/1992 | Burch |
|---|---|---|---|
| 5,176,996 | A | 1/1993 | Hogan |
| 5,294,533 | A | 3/1994 | Lupski |
| 5,627,158 | A | 5/1997 | Cho-Chung |
| 5,641,754 | A | 6/1997 | Iversen |
| 5,645,985 | A | 7/1997 | Froehler et al. |
| 5,650,316 | A | 7/1997 | Aggarwal |
| 5,683,874 | A | 11/1997 | Kool |
| 5,691,317 | A | 11/1997 | Cho-Chung |
| 5,693,773 | A | 12/1997 | Kandimalla |
| 5,780,607 | A | 7/1998 | Goodnow, Jr. |
| 5,786,138 | A | 7/1998 | Swenson |
| 5,834,185 | A | 11/1998 | Tso |
| 5,849,903 | A | 12/1998 | Pietrzkowski |
| 5,856,103 | A | 1/1999 | Gray |
| 5,869,246 | A | 2/1999 | Matsuo |
| 5,874,566 | A | 2/1999 | Veerapanane |
| 5,919,772 | A | 7/1999 | Szyf |
| 5,955,590 | A | 9/1999 | Levina |
| 5,962,426 | A | 10/1999 | Glazer |
| 5,990,088 | A | 11/1999 | Ensoli |
| 5,994,320 | A | 11/1999 | Low |
| 5,998,602 | A | 12/1999 | Torrence |
| 6,005,095 | A | 12/1999 | Capaccioli |
| 6,007,995 | A | 12/1999 | Baker |
| 6,013,522 | A | 1/2000 | Monia |
| 6,017,898 | A | 1/2000 | Pietrzkowski |
| 6,018,042 | A | 1/2000 | Mett |
| 6,025,198 | A | 2/2000 | Bennett |
| 6,033,910 | A | 3/2000 | Monia |
| 6,040,296 | A | 3/2000 | Nyce |

(Continued)

FOREIGN PATENT DOCUMENTS

| EP | 272097 | 6/1988 |
|---|---|---|
| WO | 0244321 | 6/2002 |
| WO | 2009045536 | 4/2009 |

OTHER PUBLICATIONS

Akinc, et al., "A combinatorial library of lipid-like materials for delivery of RNAi therapeutics", Nat Bioteohnol., 26 (5):561-9 (2008).

Akinc, et al., "Targeted delivery of RNAi therapeutics with endogenous and exogenous ligand-based mechanisms", Mol Ther., 18 (7):1357-64 (2010).

Astriab-Fisher, et al., "Antisense inhibition of P-glycoprotein expression using peptide-oligonucleotide conjugates", Biochem Pharmacal., 60 (I):83-90 (2000).

(Continued)

*Primary Examiner* — Janet L Epps-Smith
(74) *Attorney, Agent, or Firm* — Pabst Patent Group LLP

(57) ABSTRACT

Provided are derivatized therapeutic, prophylactic, or diagnostic agents, such as nucleic acids, that can be effectively delivered to cells and tissues. Also provided are methods of affecting a biological process by administering a therapeutic, prophylactic, or diagnostic agent, such as functional nucleic acid, to a cell or a subject, where the therapeutic, prophylactic, or diagnostic agent, such as functional nucleic acid, is derivatized therapeutic, prophylactic, or diagnostic agent, such as nucleic acid.

18 Claims, 6 Drawing Sheets

(56) References Cited

U.S. PATENT DOCUMENTS

| | | | |
|---|---|---|---|
| 6,046,004 | A | 4/2000 | Wu |
| 6,046,319 | A | 4/2000 | Power |
| 6,057,437 | A | 5/2000 | Kamiya |
| 2003/0039985 | A1* | 2/2003 | Goldsborough ....... C07H 21/00 435/6.18 |
| 2005/0119214 | A1* | 6/2005 | Manoharan ...... A61K 47/48123 514/44 A |

OTHER PUBLICATIONS

Astriab-Fisher, et al., "Conjugates of antisense oligonucleotides with the Tat and antennapedia cell-penetrating peptides: effects on cellular uptake; binding to target sequences, and biologic actions", Pharm Res., 19 (6):744-54 (2002).
Baudys, et al., "Extending Insulin Action in Vivo by Conjugation to Carboxymethyl Dextran", Bioconjugate Chem., 9:176-183 (1998).
Berman, "Insulin kinetics, models, and delivery schedules", Diabetes Care, 3:266-9 (1980).
Bernstein, et al., "Role for a bidentate ribonuclease in the initiation step of RNA interference", Nature, 409:363-6 (2001).
Browning, et al., "Prevalence of hepatic steatotis in an urban population in the United States: Impact of ethnicity", Hepatology, .40 (6):1387-95 (2004).
Caplen, et al., "Specific inhibition of gene expression by small double-stranded RNAs in invertebrate and vertebrate systems", PNAS, 98 (17):9742-7 (2001).
Cesarone, et al., "Insulin receptor substrate 1 knockdown in human MCF7 ER+ breast cancer cells by nuclease-resistant IRS1 siRNA conjugated to a disulfide-bridged D-peptide analogue of insulin-like growth factor I", Bioconjug Chem., 18 (6):1831-40 (2007).
Chen, et al., "Phenylboronic-acid-modified amphiphilic polyether as a neutral gene vector", Macromol Biosci., 12:962-9(2012).
Chiu, et al., "Visualizing a correlation between siRNA localization, cellular uptake, and RNAi in living cells", Chem Biol., 11 (8):1165-75 (2004).
Chu, et al., "Aptamer mediated siRNA delivery", Nucleic Acids Res., 34 (10):e73 (2006).
Cramer and Pugh, The influence of insulin use on glycemic control: How well do adults follow prescriptions for insulin\, Diabetes Care, 28(1):78-83 (2005).
Davidson, et al., "Highly efficient small interfering RNA delivery to primary mammalian neurons induces MicroRNA-like effects before mRNA degradation", J Neurosci., 24 (45): 10040-6 (2004).
Davis, et al., "Evidence of RNAi in humans from systemically administered siRNA via targeted nanoparticles", Nature, 464 (7291): 1067-70 (2010).
Dorsett,et al., "siRNAs: applications in funtional genomics and potential as therapeutics", Nat Rev Drug Discov, 3 (4):318-29 (2004).
Elbashir, et al., "Duplexes of 21-nucleotide RNAs mediate RNA interference in cultured mammalian cells", Nature, 411 (6836): 494-8 (2001a).
Elbashir,et al., "RNA interference is mediated by 21- and 22-nucleotide RNAs", Genes Dev., 15:188-200 (2001b).
Esposito and Giugliano, "Current insulin analogues in the treatment of diabetes: emphasis on type 2 diabetes", Expert Opin. Biol. Ther.,12:209-21 (2012).
Fire, et al., "Potent and specific genetic interference by double-stranded RNA in Caenorhabditis elegans", Nature, 391:806-11 (1998).
Gerich, "Novel insulins: expanding options in diabetes management", Am. J. Med., 113:308-316 (2002).
Gerich, "Insulin glargine: long-acting basal insulin analog for improved metabolic control", Curr. Med. Res. Opin., 20:31-7 (2004).
Hammond, et al., "An RNA-directed nuclease mediates post-transcriptional gene silencing in *Drosophila* cells", Nature, 404:293-6 (2000).

Hannon and Rossi, "Unlocking the potential of the human genome with RNA interference", Nature, 431 (7006):371-8 (2004).
Hannon, "RNA interference", Nature, 418:244-51 (2002).
Harris, et al., "Pegylation: a novel process for modifying pharmacokinetics" Clin Pharmacokinet., 40 (7):539-51 (2001).
Helms and Kelley, "Insulin glulisine: an evaluation of its pharmacodynamic properties and clinical application", Ann. Pharmacother., 43:658-68 (2009).
Hicke and Stephens, "Escort aptamers: a delivery service for diagnosis and therapy", J Clin Invest., 106 (8):923-8 (2000).
Hinds, et al., "Synthesis and Characterization of Poly(ethylene glycol)-Insulin Conjugates", Bioconjugate Chem., 11:195-201 (2000).
Ikeda, and Taira, "Ligand-targeted delivery of therapeutic siRNA", Pharm Res., 23 (8): 1631-40 (2006).
Jeong, et al., "siRNA conjugate delivery systems", Bioconjug Chem, 20 (1), 5-14 (2009).
Jinek, et al., "A programmable dual-RNA-guided DNA endonuclease in adaptive bacterial immunity", Science, 337:816-21 (2012).
Kim, et al., "Synthetic dsRNA Dicer substrates enhance RNAi potency and efficacy", Nat Bictechnol., 23 (2):222-6 (2005).
Lee, et al., "Synthesis and biological properties of insulin-deoxycholic acid chemical conjugates", Bioconjugate Chem., 16:615:20 (2005).
Leonard and Roy, "QSAR by LFER model of HIV protease inhibitor mannitol derivatives using FA-MLR, PCRA, and PLS techniques", Bioorg Med Chem., 14 (4):1039-46 (2006).
Lindgren, et al., "Cell-penetrating peptides", Trends Pharmacol Sci., 21 (3):99-103 (2000).
Lorenz, et al., "Steroid and lipid conjugates of siRNAs to enhance cellular uptake and gene silencing in liver cells", Bioorg Med Chem Lett., I4 (19):4975-7 (2004).
Love, et al., "Lipid-like materials for low-dose, in vivo gene silencing", PNAS, 107(5):1864-9 (2010).
Mahon, et al., "Combinatorial approach to determine functional group effects on lipidoid-mediated siRNA delivery", Bioconjug Chem., 21 (8):1448-54 (2010).
Maier, et al., "Synthesis of antisense Oligonucleotides conjugated a multivalent carbohydrate cluster for cellular targeting", Bioconjug Chem., 14:18-29 (2003).
Martinez, et al.,"Single-stranded antisense siRNAs guide target RNA cleavage in RNAi", Cell, 110:563-74 (2002).
McManus, et al., "Gene silencing in mammals by small interfering RNAs", Nat Rev Genet, 3 (10), 737-47 (2002).
Moffatt., et al., "Tumor-specific gene delivery mediated by a novel peptide-polyethylenimine-DNA polyplex targeting aminopeptidase N/CD13", Human Gene therapy, 16:57-67 (2005).
Moschos, et al., "Lung delivery studies using siRNA conjugated to TAT(48-60) and penetratin reveal peptide induced reduction in gene expression and induction of innate immunity", Bioconjug Chem,., 18 (5):1450-9 (2007).
Muratovska and Eccles, "Conjugate for efficient delivery of short interfering RNA (siRNA) into mammalian cells", FEBS Lett., 558 (1-3):63-8 (2004).
Naito, et al., "A phenylboronate-functionalized polyion complex micelle for ATP-triggered release of sIRNA", Angew Chem., 51:10751-5 (2012).
Napoli, et al., "Introduction of a Chimeric Chalcone Synthase Gene into Petunia Results in Reversible Co-Suppression of Homologous Genes in trans", Plant Cell, 2:279-89 (1990).
Nykanen, et al., "ATP requirements and small interfering RNA structure in the RNA interference pathway", Cell, 107:309-21 (2001).
Peng, et al., "Enhanced gene transfection capability of polyethylenimine by incorporating boronic acid groups".Chem Commun., 45:5888-90 (2010).
Phillips, et al., "Supramolecular Protein Engineering: Design of Zinc-stapled Insulin Hexamers as a Long Acting Depot", J. Bioi. Chem., 285:11755-9 (2010).
Piest and Engbersen, "Role of boronic acid moieties in poly(amido amine)s for non-viral gene delivery", J Cont Release, 155(2):331-40 (2011).

(56) References Cited

OTHER PUBLICATIONS

Pooga, et al., "Cell penetration by transportan", FASEB J., 12 (I):67-77 (1998).Prochiantz, "Messenger proteins", J Soc Biol., 194 (3-4):119-23 (2000).
Rozema, et al., "Dynamic PolyConjugates targeted in vivo delivery of siRNA to hepatocytes", PNAS, 104 (32):12982-7 (2007).
Schroeder, et al., "Lipid-based nanotherapeutics for siRNA delivery", J Intern Med., 267 (I), 9-21 (2010).
Semple, et al., "Rational design of cationic lipids for siRNA delivery", Nat Biotechnol., 28 (2): 172-6 (2010).
Shechter, et al., "Albumin-insulin conjugate releasing insulin slowly under physiological conditions: a new concept for long-acting insulin", Bioconjugate Chem., 16: 913-20 (2005).
Shechter, et al., "Reversible pegylation of insulin facilitates its prolonged action in vivo", Eur. J. Pharm. Biopharm., 70:19-28 (2008).
Siddiqui, "Insulin analogues: new dimension of management of diabetes mellitus", Mymensingh Med J., 16:117-21 (2007).
Soutschek, et al., "Therapeutic silencing of an endogenous gene by systemic administration of modified siRNAs", Nature, 432 (7014):173-8 (2004).
Stanton, et al., "Medicinal Chemistry of siRNA Delivery", J Med Chem., 53 (22):7887-901 (2010).
Szypowska, et al., "E., Long-acting insulin analogue detemir compared with NPH Insulin in type 1 diabetes. A systematic review and meta-analysis", Pol. Arch. Med. Wewn, 121:237-46 (2011).
Tripathi, et al., "Anti-HIV-I activity of anti-TAR polyamide nucleic acid conjugated with various membrane transdircing peptides", Nucleic Acids Res., 33 (13):4345-56 (2005).
Turner, et al., "Cell-penetrating peptide conjugates of peptide nucleic acids (PNA) as inhibitors of HIV-1 Tat-dependent trans-activation in cells", Nucleic Acids Res., 33 (21): 6837-49 (2005).
Turner, et al., "Synthesis, cellular uptake and HIV-I Tat-dependent trans-activalion inhibition activity of oligonucleotide analogues disulphide-conjugated to cell-penetrating peptides", Nucleic Acids Res., 33 (I):27-42 (2005b).

Ui-Tei, et al., "Sensitive assay of RNA interference in *Drosophila* and Chinese hamster cultured cells using firefly luciferase gene as target", FEBS Lett, 479:79-82 (2000).
Vaishnaw, et al., "A status report on RNAi therapeutics", Silence 1 (I):14 (2010).
Vives, et al., "A truncated HIV-I Tat protein basic domain rapidly translocates through the plasma membrane and accumulates in the cell nucleus", J Biol Chem.,272 (25):16010-7 (1997).
Wang, et al., "A peptide-targeted delivery system with pH-sensitive amphiphilic cell membrane disruption for efficient receptor-mediated sIRNA delivery", J Cont Release, 134:207-13 (2009).
Whitehead, et al., "Knocking down barriers: advances in siRNA delivery", Nat Rev Drug Discov., 8 (2):129-38 (2009).
Wolfrum, et al., "Mechanisms and optimization in vivo delivery of lipophilic siRNAs", Nat Biotechnol., 25 (10), 1149-57 (2007).
Wu, et al., "Molecular targeting and treatment of an epidermal growth factor receptor-positive glioma using boronated cetuximab", Clin Cancer Res., 13 (4):1260-8 (2007).
Xia, et al., "Intravenous sIRNA of brain cancer with receptor targeting and avidin-biotin technology", Pharm Res., 24 (12):2309-16 (2007).
Xu, et al., "Investigation of Variation in Gene Expression Profiling of Human Blood by Extended Principle Component Analysis", PLoS One, 6 (10):e26905 (2011).
Yamada, et al., "Versatile site-specific conjugation of small molecules to siRNA using click chemistry", J Org Chem., 76 (5):1198-211 (2011).
Zhang, et al., "intravenous RNA interference gene therapy targeting the human epidermal growth factor receptor prolongs survival in intracranial brain cancer", Clin Cancer Res., 10 (11):3667-77 (2004).
International Search Report for PCT/US2009/060233 dated Nov. 27, 2009.

* cited by examiner

COMPOSITIONS AND METHODS FOR FUNCTIONAL NUCLEIC ACID DELIVERY

CROSS-REFERENCE TO RELATED APPLICATIONS

This application is a 371 application of International Application No. PCT/US2013/074784, filed Dec. 12, 2013, which claims benefit and priority to U.S. Provisional Application No. 61/736,079, filed Dec. 12, 2012. International Application No. PCT/US2013/074784, filed Dec. 12, 2013 and U.S. Provisional Application No. 61/736,079, filed Dec. 12, 2012, are hereby incorporated by reference in their entirety.

FIELD OF THE INVENTION

This invention generally relates to compositions and methods for delivering nucleic acids, such as siRNA, to cells and tissues.

BACKGROUND OF THE INVENTION

Employing siRNA to induce silencing of disease-associated genes in a sequence-specific manner has considerable therapeutic promise [1, 2, 7]. Establishing affinity and specificity for a clinical target is a major challenge for conventional therapeutic approaches involving small molecules or proteins. In contrast, the generality of the endogenous RNA interference mechanism makes the silencing of any known disease-associated gene possible [7-10]. The major obstacles to the clinical implementation of siRNA therapeutics are systemic stability, immunogenicity, and intracellular delivery of nucleic acid. Recent advances have elucidated chemical modification strategies to increase nuclease resistance of administered siRNA sequences and reduce immunogenicity, but delivery remains a challenge [11]. Nanoparticle delivery systems such as liposomal formulations have demonstrated considerable in vivo efficacy, but are highly dependent on the usage of large amounts delivery material that compromise safety [2, 7, 14, 17-21]. For example, the current gold standard of efficacious liposomal siRNA delivery, C12-200, still requires a 10-fold excess of material relative to siRNA [19]. One answer to safe clinical delivery is to develop distinct chemical entities that can be attached directly to the nucleic acid and facilitate delivery while maintaining stability and low immunogenicity, thereby eliminating the need for excess delivery material. A number of small molecule and bioconjugate approaches have been attempted with mixed success, such as cholesterol-siRNA, docosamyl-siRNA, aptamers-siRNA, and TAT peptide-siRNA.

Several lipophilic small molecules have been explored as conjugates for siRNA delivery [11-13]. Attachment of cholesterol to the 3' position of the sense strand utilizing a pyrrolidine linker yielded cholesterol-siRNA conjugates with improved delivery in cultured cells. In animal experiments, cholesterol-siRNA demonstrated not only significant silencing of apoB protein levels, but also improved pharmacokinetic properties. The conjugation of several other bile acids and lipids to siRNA have also demonstrated similar improvements in both cellular uptake and pharmacokinetic properties. These improvements can be attributed to the interaction of these lipophilic moieties with lipoprotein complexes that enhance serum stability and uptake. While attachment of these lipophilic small molecules succeeded in conferring more drug-like properties, the high doses (50 mg/kg body weight) required are toxic and are a major obstacle preventing clinical implementation with these conjugates. Conjugation of siRNA to synthetic polymers bearing hepatocyte-targeting N-acetylglucosamine ligands resulted in more efficacious delivery at 2.5 mg/kg [22]. These "siRNA dynamic polyconjugates" demonstrate that attachment of large synthetic moieties can achieve reasonable dosing with low toxicity. However, this technology relies on targeting ligands for efficacy and is currently limited to hepatocyte delivery.

Cell-penetrating peptides are highly effective delivery agents that have been implemented successfully as delivery vehicles for proteins, antisense oligonucleotides, and peptide-like nucleic acids [8, 23-36]. TAT trans-activator protein (48-60), transportan, and penetratin are popular cell-penetrating peptides that have been evaluated as potential siRNA delivery conjugates [23, 29, 31, 34, 35]. Peptides were conjugated to the 3' position of the antisense siRNA strand via a reducible disulfide linkage, giving these conjugates the added potential of removal inside the reducing environment of the cytoplasm after delivery. These peptide-siRNA conjugates demonstrated highly efficacious delivery in cultured cells and down-regulated target genes in mouse models. However, the peptides did not improve in vivo stability, with peptide-siRNA conjugates exhibiting clearance rates similar to naked siRNA. In addition, certain cell-penetrating peptides induced inflammatory and immunogenic responses that would be problematic in a therapeutic context [29].

A number of bioconjugates have also been investigated for their ability to enhance siRNA delivery [37-39]. Receptor ligand-mediated delivery was explored by attachment of insulin growth factor 1 (IGF1) peptide to siRNA [37]. While delivery was improved relative to naked siRNA, this conjugate system could not surpass cholesterol-siRNA for efficacy. While aptamers-conjugated siRNA have demonstrated targeting and improved transfection in proof-of-concept studies, they lack systemic stability, are highly prone to nuclease degradation, and may be unable to induce efficient endosomal escape [40, 41]. Antibody-based targeting systems have received attention for their specificity and high systemic stability and have shown some promising results in an implanted rat tumor model [42, 43]. However, these systems still contend with immunogenicity.

A viable siRNA conjugate system that facilitates delivery without compromising stability or immunogenicity has yet to be identified.

Thus, it is an object of this invention to provide siRNA conjugates that efficiently deliver the siRNA to cells with acceptable stability and immunogenicity.

It is also an object of this invention to provide methods of siRNA treatment using siRNA conjugates that efficiently deliver the siRNA to cells with acceptable stability and immunogenicity.

It is also an object of this invention to provide methods of optimizing siRNA delivery through combination of moieties having different chemical and physical properties.

It is also an object of this invention to provide a compositions for effective delivery of nucleic acids, such as siRNA, to cells and tissues.

It is a further objection of this t invention to provide methods of effectively delivering nucleic acids, such as siRNA, to cells and tissues.

SUMMARY OF THE INVENTION

Therapeutic, prophylactic, or diagnostic agents, such as functional nucleic acids, derivatized with an oligomer are provided. The oligomer is made up of monomers that can have modified sidechains providing a variety of chemical and physical properties that can affect delivery in vivo.

For example, derivatized agents, such as functional nucleic acids, are provided that are made up of the agent conjugated to an oligomer of 2 to 5 monomer residues. The monomers are made up of single modified sidechains, dual modified sidechains, or combinations thereof. The side chains are modified with a phenylboronic acid group, hydrophobic residues, hydrophilic residues, charged residues, diol residues, fluorescent residues, and combinations thereof.

In some embodiments, the sidechains are modified with nonpolar cyclic hydrocarbon residues, nonpolar acyclic hydrocarbon residues, tertiary amine residues, cyclic amine residues, cyclic neutral hydrophilic residues, and acyclic neutral hydrophilic residues.

In some embodiments, each monomer residue of the oligomer is —CO—O—$R_3$—, where $R_3$ is —$CR_4$—$(CH_2)_m$—NH— or pyrrolidine substituted with $R_4$, wherein m is an integer from 0 to 25, where $R_4$ is —CO—NH—$R_5$ or —CO—NH—C(CH—CO—NH—$R_5)_2$, and where each $R_5$ is independently a hydrophobic residue, a hydrophilic residue, a neutral residue, an amine-containing residue, a charged residue, or a fluorescent residue.

In some embodiments, each $R_5$ is independently a nonpolar cyclic hydrocarbon residue, a nonpolar acyclic hydrocarbon residue, a tertiary amine residue, a cyclic amine residue, a cyclic neutral hydrophilic residue, or a acyclic neutral hydrophilic residue.

In some embodiments, each monomer residue of the oligomer is —CO—O—$R_3$—, where $R_3$ is —$CR_4$—$(CH_2)_m$—NH— or pyrrolidine substituted with $R_4$, where m is an integer from 0-25, $R_4$ is —CO—NH—$R_5$ or —CO—NH—C(CH—CO—NH—$R_5)_2$, and $R_5$ is the side chain modification. In some embodiments, $R_5$ is a phenylboronic acid group, $C_{8-18}$ alkyl, —$CH_2$-phenyl, —$(CH_2$—$CH_2$—O$)_p$—H or —$(CH_2$—$CH_2$—O$)_p$—$CH_3$, wherein p is an integer from 1-500, —$CH_2$-dioxane, —$CH_2$—$CH_2$-oxazane, —$CH_2$—$CH_2$—N($CH_2$—$CH_3)_2$, —$CH_2$—$CH_2$-pyrazole, a fluorescent group, -piperidine-phenyl, -piperidine-oxazane, -piperidine-$CH_2$—$CH_2$—N($CH_2$—$CH_3)_2$, -piperidine-$CH_2$—$CH_2$-pyrazole, -dimethylaminobenzyl, or -pyridine. At least one $R_5$ is a phenylboronic acid group.

In some embodiments, the therapeutic, prophylactic, or diagnostic agent is a functional nucleic acid. In some embodiments, the functional nucleic acid is an siRNA, an aptamer, an antisense nucleic acid, an shRNA, a ribozyme, a triplex forming molecule, CRISPR (Clustered Regularly Interspaced Short Palindromic Repeats) RNA (crRNA), or an external guide sequence.

Also provided are methods of treating a subject by administering to the subject a derivatized therapeutic, prophylactic, or diagnostic agent, such as functional nucleic acid wherein the derivatized agent affects a biological process of the subject.

Also provided are methods of affecting a biological process by administering a derivatized therapeutic, prophylactic, or diagnostic agent, such as functional nucleic acid, to a cell or a subject.

Also provided are methods of making a derivatized therapeutic, prophylactic, or diagnostic agent, such as functional nucleic acid, comprising: (i) reacting a first monomer with a second monomer, where the monomers each comprise an amine moiety, an alcohol moiety, and a modified sidechain, where the alcohol moiety of the first monomer and the amine moiety of the second monomer are linked via a carbamate reaction to produce a dimer; (ii) reacting the dimer with a third monomer, where the third monomers comprises an amine moiety, an alcohol moiety, and a modified sidechain, where the alcohol moiety of the dimer and the amine moiety of the third monomer are linked via a carbamate reaction to produce a trimer; (iii) reacting the trimer with an azide-containing group, where the azide-containing group comprises and azide moiety and an alcohol moiety, where the alcohol moiety of the azide-containing moiety and the amine moiety of the first monomer are linked via a carbamate reaction to produce an azide-trimer; and (iv) reacting the azide-trimer with an alkyne-derivatized agent, where the azide moiety and the alkyne moiety of the alkyne-derivatized agent are linked to produce the derivatized agent (such as a derivatized functional nucleic acid).

In some embodiments, step (i) is performed a plurality of times using a different first monomer, a different second monomer, or different first and second monomers. In some embodiments, step (ii) is performed a plurality of times using a different dimer, a different third monomer, or a different dimer and a different third monomer.

In some embodiments, the monomers are prepared by reacting a monomer backbone with a sidechain modifying group, where the monomer backbone comprises a carboxylic acid moiety, an amine moiety, and an alcohol moiety, and where the sidechain modifying group comprises an amine group, wherein the sidechain modifying group amidates the carboxylic acid moiety via the amine group.

In some embodiments, the sidechain modifying groups are independently a hydrophobic residue, a hydrophilic residue, a neutral residue, an amine-containing residue, a charged residue, or a fluorescent residue.

In some embodiments, the sidechain modifying groups are independently a nonpolar cyclic hydrocarbon residue, a nonpolar acyclic hydrocarbon residue, a tertiary amine residue, a cyclic amine residue, a cyclic neutral hydrophilic residue, or an acyclic neutral hydrophilic residue.

In some embodiments, the method further includes (v) testing the derivatized therapeutic, prophylactic, or diagnostic agent, such as functional nucleic acid, for function, stability, immunogenicity, or a combination, where function of the derivatized agent above a threshold, stability of the derivatized agent above a threshold, immunogenicity below a threshold, or a combination, identifies the derivatized agent as useful for delivery of the agent.

Also disclosed are derivatized therapeutic, prophylactic, or diagnostic agents, such as derivatized functional nucleic acids, made by the provided methods.

DETAILED DESCRIPTION OF THE INVENTION

Figure 1A:
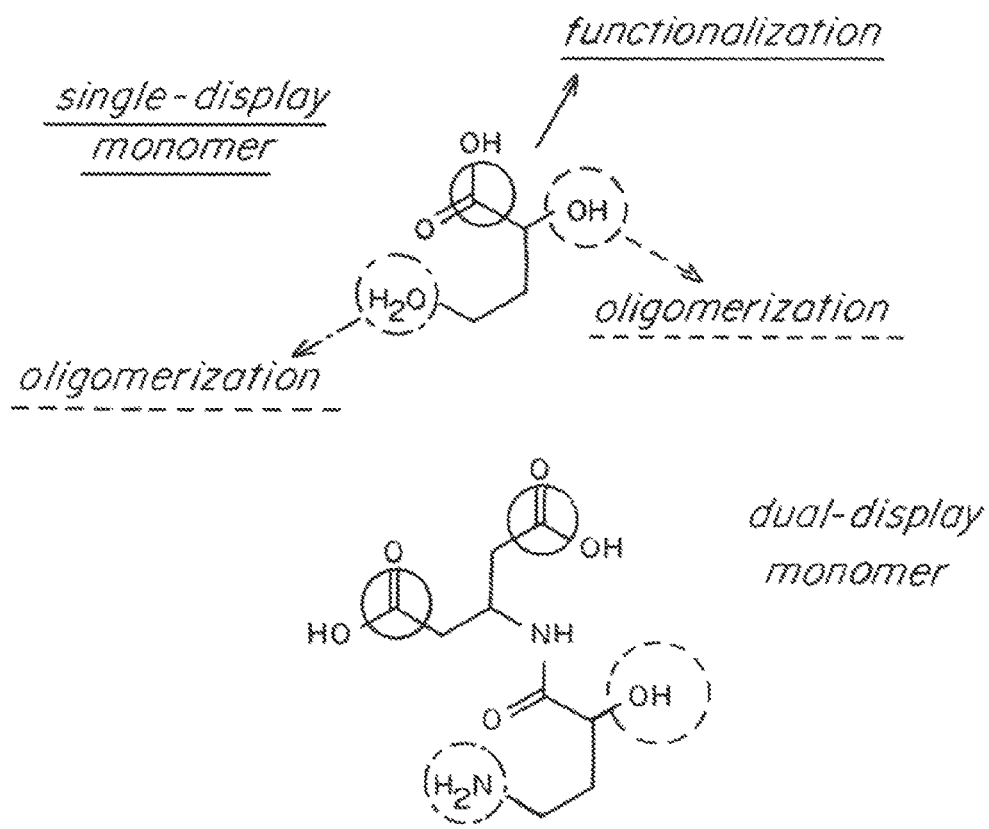
FIGS. 1A-1E are diagrams showing examples of monomer design, oligomer synthesis, and conjugation of oligomers to siRNA. (a) Amine, alcohol, and carboxylic acid moieties are used for monomer functionalization and controlled oligomerzation. Amine and alcohol moieties can be used for oligomerization, while carboxylic acid moieties are used for functionalization of the monomers. (b) Examples of delivery-relevant functionalities for monomer functionalization. (c) Representative structures of functionalized monomers. (d) Synthetic strategy used in oligomeric synthesis. (e) Successful conlugation of oligomeric sequencesto dibenzocyclooctyne siRNA utilizing copper-free Huisgen cycloaddition.

To realize the potential of siRNA with delivery agents as a means to improve clinical outcomes, a fully synthetic and oligomeric conjugate system was developed to safely and efficiently deliver siRNA in vivo. These oligomers are designed to combine the low immunogenicity of small molecules with the efficacy of peptides. It was realized that a mix of lipophilic, hydrophilic, and pH-dependent alkali moieties used in nanoparticle formulations for nucleic acid delivery [7, 9, 14] are useful to overcoming cellular delivery barriers. The oligomeric conjugates incorporate these delivery-biasing functionalities into a defined set of monomers that are the building blocks for oligomer synthesis.

I. Definitions

The term siRNA refers to a small interfering RNA, commonly 18 to 30 nucleotides, preferably 20 to 25, more preferably 21 to 23, or approximately 22 nucleotide double-stranded RNA. Preferably at least one strand has a 5'- and/or 3' overhang of 1 to 5, preferably 1 to 3, or 2 nucleotides. siRNA is involved in the RNA interference pathway where the siRNA interferes with the expression of a specific gene.

The term shRNA refers to short hairpin RNA, an RNA structure that forms a tight hairpin turn, which can also be used to silence gene expression via RNA interference. The shRNA hairpin structure is cleaved by the cellular machinery into small interfering RNA (siRNA), which is then bound to the RNA-induced silencing complex (RISC). This complex binds to and cleaves mRNA, which matches the siRNA that is bound to it.

"Dosage unit form" as used herein refers to a physically discrete unit of conjugate appropriate for the patient to be treated.

"Hydrophilic," as used herein, refers to molecules which have a greater affinity for, and thus solubility in, water as compared to organic solvents. The hydrophilicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the water than in the organic solvent, then the compound is considered hydrophilic.

"Hydrophobic," as used herein, refers to molecules which have a greater affinity for, and thus solubility in, organic solvents as compared to water. The hydrophobicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the organic solvent than in the water, then the compound is considered hydrophobic.

"Neutral," as used herein, refers to molecules which do not have a charge under the relevant conditions. Absent specified conditions, the conditions are neutral pH in water.

"Charged," as used herein, refers to molecules which have a charge under the relevant conditions. Absent specified conditions, the conditions are neutral pH in water. The charge can be positive, negative, or both (on different portions of the molecule).

"Nonpolar," as used herein, refers to molecules which do not have a significant dipole under the relevant conditions. Absent specified conditions, the conditions are neutral pH in water.

"Polar," as used herein, refers to molecules which have a significant dipole under the relevant conditions. Absent specified conditions, the conditions are neutral pH in water.

"Peptide," as used herein includes "polypeptide," "oligopeptide," and refers to a chain of at α-amino acid residues linked together by covalent bonds (e.g., peptide bonds). The length of the peptide is limited at the lower end only by the minimum number amino acids required to form a self-assembling peptide.

"Pharmaceutically acceptable carrier" as used herein means a non-toxic, inert solid, semi-solid or liquid filler, diluent, encapsulating material or excipient. Remington's Pharmaceutical Sciences Ed. by Gennaro, Mack Publishing, Easton, Pa., current edition, discloses various carriers used in formulating pharmaceutical compositions and known techniques for the preparation thereof.

The term "oligomeric", as used herein, describes something made primarily from a plurality of monomeric units and is generally referred to as an "oligomer." An oligomer can have a molecular weight between 10 Daltons and 15,000 Daltons, between 100 Daltons and 10,000 Daltons, or between 500 Daltons and 5,000 Daltons. An oligomer can have from 3 to 100 monomeric units, from 4 to 50 monomeric units, or from 5 to 25 monomeric units.

"Biocompatible" and "biologically compatible," as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory, immune or toxic response when administered to an individual.

The expression "an amino acid residue having a carboxylic acid group in the side chain" designates amino acid residues like Asp, Glu and hGlu. The amino acids can be in either the L- or D-configuration. If nothing is specified it is understood that the amino acid residue is in the L configuration.

The expression "an amino acid residue having a neutral side chain" designates amino acid residues like Gly, Ala, Val, Leu, Ile, Phe, Pro, Ser, Thr, Cys, Met, Tyr, Asn and Gln.

By "activated acid" is meant a carboxylic acid in which an activated leaving group has been attached to the acyl carbon enabling reaction with an amino group under formation of an amide bond and release of the leaving group. Activated fatty acids may be activated esters of fatty acids, activated amides of fatty acids and anhydrides or chlorides. Activated fatty acid includes derivatives thereof such as N-hydroxybenzotriazole and N-hydroxysuccinimide.

By "fatty acid" is meant a linear or branched carboxylic acids having at least 2 carbon atoms and being saturated or unsaturated. Examples of fatty acids are capric acid, lauric acid, tetradecanoic acid (myristic acid), pentadecanoic acid, palmitic acid, heptadecanoic acid, and stearic acid.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$ and the preferred ranges discussed above) and possible substitution to the alkyl groups described above.

"Aryl", as used herein, refers to 5-, 6- and 7-membered aromatic ring. The ring may be a carbocyclic, heterocyclic, fused carbocyclic, fused heterocyclic, bicarbocyclic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro [2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

When a compound is stated to be "soluble at physiological pH values" it means that the compound can be used for preparing compositions that are fully dissolved at physiological pH values. Such favorable solubility may either be due to the inherent properties of the compound alone or a result of a favorable interaction between the compound and one or more ingredients contained in the vehicle.

The term "sidechain" as used herein refers to a chemical group linked to a backbone, chain, or polymer. For example, sidechains are used herein to derivatize monomers and oligomers.

II. Compositions

A. Monomers

Monomers are used to make oligomers to aid in delivery of therapeutic, prophylactic, or diagnostic agents, such as functional nucleic acids (such as siRNA). Use of monomers and oligomerization allow a variety of chemical and physical properties to be combined easily in a delivery-relevant oligomer. For this purpose, it is useful for the monomers to have a backbone framework which can be modified with a variety of sidechains having a variety of chemical and physical properties. For ease of assembling monomers and oligomers, it is useful to use monomer backbone frameworks that include three different reactive groups, where each different group allows directed functionalization and oligomerization of the monomer. As used herein, "monomer backbone framework" and "monomer backbone" refer to the core structure of a monomer that is yet to be derivatized or oligomerized.

Generally, the monomers can have single modified sidechains or dual modified sidechains. Monomers with single modified sidechains have a single modified sidechain and monomers with dual modified sidechains have two modified sidechains. Correspondingly, the monomer backbone framework for monomers with single modified sidechains have a single reactive moiety for derivatization of the monomer backbone framework and monomers with dual modified sidechains have two reactive moieties for derivatization of the monomer backbone framework.

Preferred reactive groups for oligomerization are amine groups and hydroxyl groups. These allow carbamate oligomerization of monomers and facilitate derivativization of the ends of oligomers. A preferred reactive group for derivatization of monomers with modified side chains are carboxylic acid groups. Numerous other reactive groups are known and can be used for oligomerization and derivatization of monomers.

B. Modified Sidechain Groups

Modified sidechain groups, sidechain groups, or sidechains are chemical groups linked to a backbone, chain, or polymer. For example, sidechains are used herein to derivatize monomers and oligomers. The sidechains can be any chemical groups suitable to the purpose of the molecules and compositions in which they are used. For the monomers, oligomers, and derivatized therapeutic, prophylactic, or diagnostic agents, such as derivatized functional nucleic acids, herein, it is useful to use a fixed set of modified sidechain groups. Generally, the set of sidechains can be selected to include chemical groups with a variety of chemical and physical properties, such as delivery-relevant properties.

For example, the modified sidechain groups can be hydrophobic residues, hydrophilic residues, neutral residues, amine-containing residues, charged residues, fluorescent residues, or combinations thereof. As another example, the modified sidechain groups can be nonpolar cyclic hydrocarbon residues, nonpolar acyclic hydrocarbon residues, tertiary amine residues, cyclic amine residues, cyclic neutral hydrophilic residues, and acyclic neutral hydrophilic residues.

An example of a useful set of modified sidechain groups is a phenylboronic acid group, $C_{8-18}$ alkyl, —$CH_2$-phenyl, —(CH$_2$—CH$_2$—O)$_p$—H or —(CH$_2$—CH$_2$—O)$_p$—CH$_3$, wherein p is an integer from 1-500, —CH$_2$-dioxane, —CH$_2$—CH$_2$-oxazane, —CH$_2$—CH$_2$—N(CH$_2$—CH$_3$)$_2$, —CH$_2$—CH$_2$-pyrazole, a fluorescent group, -piperidine-phenyl, -piperidine-oxazane, -piperidine-CH$_2$—CH$_2$—N(CH$_2$—CH$_3$)$_2$, -piperidine-CH$_2$—CH$_2$-pyrazole, -dimethyl-aminobenzyl, or -pyridine.

C. Oligomers

Oligomers of the monomers are useful to aid in delivery of therapeutic, prophylactic, or diagnostic agents, such as functional nucleic acids (such as siRNA), which are conjugated to the oligomers. By combining in oligomers monomers having a variety of chemical and physical properties, such as delivery-relevant properties, the effectiveness of delivery of the oligomers can be increased. For this purpose, it is useful for the oligomers to be easily derivatized with the therapeutic, prophylactic, or diagnostic agent.

Generally, oligomers can have from two to five monomers. Preferred oligomers have a molecular weight of between 0.9 and 1.8 of the molecular weight of the agent. For example, the oligomer can have a molecular weight of about 1.1 of the molecular weight of the therapeutic, prophylactic, or diagnostic agent.

D. Derivatized Therapeutic, Prophylactic, and Diagnostic Agents

The compositions described herein can be used for the effective delivery of one or more therapeutic, prophylactic, or diagnostic agents, such as functional nucleic acids (such as siRNA). In some embodiments the compositions contain only a single therapeutic, prophylactic, or diagnostic agent. In other embodiments multiple agents can be delivered, either together or independently. Preferred therapeutic, prophylactic, or diagnostic agents are functional nucleic acids. Preferred functional nucleic acids are siRNA.

Derivatized therapeutic, prophylactic, or diagnostic agents, such as functional nucleic acids (such as derivatized siRNA), are conjugates of an oligomer and a therapeutic, prophylactic, or diagnostic agent. A therapeutic, prophylactic, or diagnostic agent, such as functional nucleic acid, can be derivatized with an oligomer in any suitable way. Generally, the oligomer will have a reactive group that facilitates derivatization to the agent. The therapeutic, prophylactic, or diagnostic agent can have or can be modified to include a corresponding reactive group. Preferably, the reactive groups for derivatizing a therapeutic, prophylactic, or diagnostic agent with an oligomer can be reactive groups used in click chemistry. For example, an azide moiety and an alkyne moiety can be used. Numerous other reactive groups are known and can be used for derivatization of therapeutic, prophylactic, or diagnostic agents.

E. Functional Nucleic Acids

Functional nucleic acids can be derivatized as described herein to aid in their delivery. Derivatization of a nucleic acid can provide nucleic acids with useful properties, such as improved stability, targeting, and half-life.

Functional nucleic acids are nucleic acid molecules that have a specific function, such as binding a target molecule, serving as an enzyme substrate or cofactor, or catalyzing a specific reaction. For example, functional nucleic acids can bind a target nucleic acid (RNA or DNA) or can serve as enzyme substrate-guiding sequence (or guide). Functional nucleic acid molecules can be divided into the following categories, which are not meant to be limiting. For example, functional nucleic acids include antisense molecules, aptamers, ribozymes, triplex forming molecules, RNA interference (RNAi), CRISPR (Clustered Regularly Interspaced Short Palindromic Repeats) RNA (crRNA), and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Often functional nucleic acids are designed to interact with other nucleic acids based on sequence complementarity between the target molecule and the functional nucleic acid molecule. In other situations, the specific recognition between the functional nucleic acid molecule and the target molecule is not based on sequence complementarity between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNase H mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$. A representative sample of methods and techniques which aid in the design and use of antisense molecules can be found in U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than 10-6, 10-8, 10-10, or 10-12. Representative examples of how to make and use triplex forming molecules to bind a variety of different target molecules can be found in U.S. Pat. Nos. 5,176,996, 5,645,985, 5,650,316, 5,683,874, 5,693,773, 5,834,185, 5,869,246, 5,874,566, and 5,962,426. Gene expression can also be effectively silenced in a highly specific manner through RNA interference (RNAi). This silencing was originally observed with the addition of double stranded RNA (dsRNA) (Fire, A., et al., Nature, 391:806-11 (1998); Napoli, C., et al., Plant Cell, 2:279-89 (1990); Hannon, G. J., Nature, 418:244-51 (2002)). Once dsRNA enters a cell, it is cleaved by an RNase III-like enzyme, Dicer, into double stranded small interfering RNAs (siRNA) 21-23 nucleotides in length that contain 2 nucleotide overhangs on the 3' ends (Elbashir, S. M., et al., Genes Dev., 15:188-200 (2001);

Bernstein, E., et al., Nature, 409:363-6 (2001); Hammond, S. M., et al., Nature, 404:293-6 (2000)). In an ATP-dependent step, the siRNAs become integrated into a multi-subunit protein complex, commonly known as the RNAi induced silencing complex (RISC), which guides the siRNAs to the target RNA sequence (Nykanen, A., et al., Cell, 107:309-21 (2001)). At some point the siRNA duplex unwinds, and it appears that the antisense strand remains bound to RISC and directs degradation of the complementary mRNA sequence by a combination of endo and exo-nucleases (Martinez, J., et al., Cell, 110:563-74 (2002)). However, the effect of RNAi or siRNA or their use is not limited to any type of mechanism.

Small Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al., Nature, 411:494 498(2001); Ui-Tei, K., et al., FEBS Lett, 479:79-82 (2000)). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

Similar to RNAi, CRISPR (Clustered Regularly Interspaced Short Palindromic Repeats) interference is a powerful approach, via selective DNA cleavage, for reducing gene expression of endogenously expressed proteins. CRISPRs are genetic elements containing direct repeats separated by unique spacers, many of which are identical to sequences found in phage and other foreign genetic elements. Recent work has demonstrated the role of CRISPRs in adaptive immunity and shown that small RNAs derived from CRISPRs (crRNAs) are implemented as homing oligonucleotides for the targeted interference of foreign DNA (Jinek et al., Science, 337:816-821 (2012)). crRNAs are used to selectively cleave DNA at the genetic level.

Where the functional nucleic acid serves as an enzyme cofactor, the cofactor can be, for example, a substrate-guiding sequence (or guide), which directs a nuclease to cleave a substrate (an RNA or DNA).

F. Pharmaceutical Compositions

Pharmaceutical compositions containing a therapeutic, prophylactic, or diagnostic agent derivative, such as functional nucleic acid derivative, may be administered parenterally to subjects in need of such a treatment. Parenteral administration can be performed by subcutaneous, intramuscular or intravenous injection by means of a syringe, optionally a pen-like syringe. Alternatively, parenteral administration can be performed by means of an infusion pump. Further options are to administer the therapeutic, prophylactic, or diagnostic agent nasally or pulmonally, preferably in compositions, powders or liquids, specifically designed for the purpose.

Injectable compositions of the therapeutic, prophylactic, or diagnostic agent derivatives can be prepared using the conventional techniques of the pharmaceutical industry which involve dissolving and mixing the ingredients as appropriate to give the desired end product. Thus, according to one procedure, a therapeutic, prophylactic, or diagnostic agent derivative can be dissolved in an amount of water which is somewhat less than the final volume of the composition to be prepared. An isotonic agent, a preservative and a buffer can be added as required and the pH value of the solution is adjusted—if necessary—using an acid, e.g., hydrochloric acid, or a base, e.g., aqueous sodium hydroxide, as needed. Finally, the volume of the solution can be adjusted with water to give the desired concentration of the ingredients.

In some embodiments, the buffer can be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers and their combinations constitutes an alternative embodiment.

In some embodiments, the formulation can further comprise a pharmaceutically acceptable preservative which can be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In some embodiments, the preservative can be present in a concentration from 0.1 mg/ml to 20 mg/ml. In some embodiments, the preservative can be present in a concentration from 0.1 mg/ml to 5 mg/ml. In some embodiments, the preservative can be present in a concentration from 5 mg/ml to 10 mg/ml. In some embodiments, the preservative can be present in a concentration from 10 mg/ml to 20 mg/ml. Each one of these specific preservatives and their combinations constitutes an alternative embodiment. The use of a preservative in pharmaceutical compositions is well-known to the skilled person. For convenience reference is made to Remington: *The Science and Practice of Pharmacy*, current edition.

In some embodiments, the formulation can further comprise an isotonic agent which can be selected from the group consisting of a salt (e.g., sodium chloride), a sugar or sugar alcohol, an amino acid (e.g., glycine, L-histidine, arginine, lysine, isoleucine, aspartic acid, tryptophan, threonine), an alditol (e.g., glycerol (glycerine), 1,2-propanediol (propyleneglycol), 1,3-propanediol, 1,3-butanediol)polyethyleneglycol (e.g., PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In some embodiments, the sugar additive can be sucrose. Sugar alcohol is defined as a $C_4$-$C_8$ hydrocarbon having at least one —OH group and includes, for example, mannitol, sorbitol, inositol, galactitol, dulcitol, xylitol, and arabitol. In some embodiments, the sugar alcohol additive can be mannitol. The sugars or sugar alcohols mentioned above can be used individually or in combination. There is no fixed limit to the amount used, as long as the sugar or sugar alcohol is soluble in the liquid preparation and does not adversely affect the effects achieved using the therapeutic, prophylactic, or diagnostic agent derivatives (such as delivery efficaciousness). In some embodiments, the sugar or sugar alcohol concentration can be between about 1 mg/ml and about 150 mg/ml. In some embodiments, the isotonic agent can be present in a concentration from 1 mg/ml to 50 mg/ml. In some embodiments, the isotonic agent can be present in a concentration from 1 mg/ml to 7 mg/ml. In some embodiments, the isotonic agent can be present in a concentration from 8 mg/ml to 24 mg/ml. In some embodiments, the isotonic agent can be present in a concentration from 25 mg/ml to 50 mg/ml. Each one of these specific isotonic agents and their combinations constitutes an alternative embodiment. The use of an isotonic agent in pharmaceutical compositions is well-known.

Typical isotonic agents are sodium chloride, mannitol, dimethyl sulfone and glycerol and typical preservatives are phenol, m-cresol, methyl p-hydroxybenzoate and benzyl alcohol. Examples of suitable buffers are sodium acetate, glycylglycine, HEPES (4-(2-hydroxyethyl)-1-piperazineethanesulfonic acid) and sodium phosphate.

A composition for nasal administration of a therapeutic, prophylactic, or diagnostic agent derivative can, for example, be prepared as described in European Patent No. 272097 (to Novo Nordisk A/S).

Compositions containing therapeutic, prophylactic, or diagnostic agent derivatives can be used in the treatment of states which are sensitive to the therapeutic, prophylactic, or diagnostic agent. The optimal dose level for any subject will depend on a variety of factors including the efficacy of the specific therapeutic, prophylactic, or diagnostic agent derivative employed, the age, body weight, physical activity, and diet of the patient, on a possible combination with other drugs, and on the severity of the state to be treated. It is recommended that the daily dosage of the therapeutic, prophylactic, or diagnostic agent derivative be determined for each individual subject by those skilled in the art.

In some embodiments, a pharmaceutical composition comprising a therapeutically effective amount of a therapeutic, prophylactic, or diagnostic agent derivative, such as functional nucleic acid derivative, together with a pharmaceutically acceptable carrier can be provided for treatment in a subject in need of such a treatment. A therapeutic, prophylactic, or diagnostic agent derivative can be used for the manufacture of a pharmaceutical composition for use in the treatment.

In some embodiments, a therapeutic, prophylactic, or diagnostic agent derivative, such as a functional nucleic acid derivative, which is soluble at physiological pH values is provided. In some embodiments, a therapeutic, prophylactic, or diagnostic agent derivative which is soluble at pH values in the interval from about 6.5 to about 8.5 is provided.

In some embodiments, a pharmaceutical composition comprising a therapeutic, prophylactic, or diagnostic agent derivative, such as functional nucleic acid derivative, which is soluble at physiological pH values is provided. In some embodiments, a pharmaceutical composition comprising a therapeutic, prophylactic, or diagnostic agent derivative which is soluble at pH values in the interval from about 6.5 to about 8.5 is provided.

In some embodiments, a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of a therapeutic, prophylactic, or diagnostic agent derivative.

In some embodiments, a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of a functional nucleic acid derivative.

The compositions described herein can be used for the delivery of one or more therapeutic, prophylactic, or diagnostic agents. In some embodiments the compositions contain only a single therapeutic, prophylactic, or diagnostic agent, e.g., a single functional nucleic acid. In other embodiments multiple agents can be delivered, either together or independently. For example, in some embodiments it can be advantageous to provide delivery of a first therapeutic, prophylactic, or diagnostic agent, while at the same time providing for delivery of a second therapeutic, prophylactic, or diagnostic agent.

II. Methods of Making Delivery Compositions

A. Methods of Making Derivatized Therapeutic, Prophylactic, or Diagnostic Agents Therapeutic, prophylactic, or diagnostic agents, such as functional nucleic acids, can be derivatized using any suitable techniques. The starting product for the acylation of the parent therapeutic, prophylactic, or diagnostic agent or a precursor thereof can be produced by either well-known organic synthesis or by well-known in vitro and recombinant production in suitable transformed microorganisms. Thus the therapeutic, prophylactic, or diagnostic agent starting product can be produced by a method which comprises culturing a host cell containing a DNA sequence encoding the nucleic acid (or that embodies the nucleic acid).

Derivatized therapeutic, prophylactic, or diagnostic agents, such as derivatized functional nucleic acids, can be made by, for example, (i) reacting a first monomer with a second monomer, where the monomers each comprise an amine moiety, an alcohol moiety, and a modified sidechain, where the alcohol moiety of the first monomer and the amine moiety of the second monomer are linked via a carbamate reaction to produce a dimer; (ii) reacting the dimer with a third monomer, where the third monomers comprises an amine moiety, an alcohol moiety, and a modified sidechain, where the alcohol moiety of the dimer and the amine moiety of the third monomer are linked via a carbamate reaction to produce a trimer; (iii) reacting the trimer with an azide-containing group, where the azide-containing group comprises and azide moiety and an alcohol moiety, where the alcohol moiety of the azide-containing moiety and the amine moiety of the first monomer are linked via a carbamate reaction to produce an azide-trimer; and (iv) reacting the azide-trimer with an alkyne-derivatized therapeutic, prophylactic, or diagnostic agent, such as alkyne-derivatized functional nucleic acid, where the azide moiety and the alkyne moiety of the alkyne-derivatized agent are linked to produce the derivatized therapeutic, prophylactic, or diagnostic agent.

This method can be used to produce combinatorial sets of monomers. For example, step (i) can be performed a plurality of times using a different first monomer, a different second monomer, or different first and second monomers. Similarly, step (ii) can be performed a plurality of times using a different dimer, a different third monomer, or a different dimer and a different third monomer. The result can be complete or partial sets of all of the monomers being used embodied in permutations of trimmers.

The different monomers can be made by, for example, reacting a monomer backbone with a sidechain modifying group, where the monomer backbone comprises a carboxylic acid moiety, an amine moiety, and an alcohol moiety, and where the sidechain modifying group comprises an amine group, wherein the sidechain modifying group amidates the carboxylic acid moiety via the amine group.

The sidechain modifying groups that are used define the chemical and physical properties of the resulting monomers and oligomers. Relevant to delivery, the sidechain modifying groups cam be independently a hydrophobic residue, a hydrophilic residue, a neutral residue, an amine-containing residue, a charged residue, or a fluorescent residue. The sidechain modifying groups can be independently a nonpolar cyclic hydrocarbon residue, a nonpolar acyclic hydrocarbon residue, a tertiary amine residue, a cyclic amine residue, a cyclic neutral hydrophilic residue, or an acyclic neutral hydrophilic residue.

Producing a combinatorial library of oligomers that are conjugated to therapeutic, prophylactic, or diagnostic agents, such as functional nucleic acids, allows testing of the derivatized agents to identify oligomers useful for delivery of the agents. For example, the derivatized therapeutic, prophylactic, or diagnostic agent can be tested for function, stability, immunogenicity, or a combination, where function of the derivatized therapeutic, prophylactic, or diagnostic agent above a threshold, stability of the derivatized therapeutic, prophylactic, or diagnostic agent above a threshold, immunogenicity below a threshold, or a combination, identifies the derivatized therapeutic, prophylactic, or diagnostic agent as useful for delivery of the therapeutic, prophylactic, or diagnostic agent.

B. Dosage Forms

Dosage forms may be formulated in a conventional manner using one or more physiologically acceptable carriers comprising known excipients and auxiliaries which facilitate processing into preparations which can be used pharmaceutically. In one embodiment, prior to injection, the formulation is in the form of a suspension.

Formulation of drugs is discussed in, for example, Hoover, John E., Remington's Pharmaceutical Sciences, Mack Publishing Co., Easton, Pa. (current edition), and Liberman, H. A. and Lachman, L., Eds., Pharmaceutical Dosage Forms, Marcel Decker, New York, N.Y. (1980). Proper formulation is dependent upon the route of administration chosen.

In a preferred embodiment, the formulation is an injectable formulation. An injectable therapeutic, prophylactic, or diagnostic agent, such as functional nucleic acid, formulation can be made by suspending the therapeutic, prophylactic, or diagnostic agent derivative in a diluent. The suspension is sterilized and filled in a vial suitable for unit or multiple injection dosing. Sterile injectable preparations may be formulated as known in the art. Among the acceptable vehicles and solvents that may be employed are water, Ringer's solution, U.S.P. and isotonic sodium chloride solution. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use. Components and compositions for such formulations are described further elsewhere herein.

IV. Methods of Using Compositions

Derivatized therapeutic, prophylactic, or diagnostic agents, such as derivatized functional nucleic acid, can be used for delivery of the therapeutic, prophylactic, or diagnostic agents to cells in tissues. For example, derivatized agents can be used to treat a subject by administering to the subject the derivatized agent, where the derivatized agent affects a biological process of the subject.

Nucleic acids are polymeric macromolecules, essential for all known forms of life. Nucleic acids, which include deoxyribonucleic acid (DNA) and ribonucleic acid (RNA), are made from monomers known as nucleotides. Each nucleotide has three components: a 5-carbon sugar, a phosphate group, and a nitrogenous base. If the sugar is deoxyribose, the polymer is DNA. If the sugar is ribose, the polymer is RNA.

RNA can also include noncoding RNA (ncRNA), such as small interfering RNA (siRNA), micro RNA (miRNA), ribosomal RNA (rRNA), transfer RNA (tRNA), small nucleolar RNA (snoRNA), short hairpin RNA (shRNA), and small nuclear RNA (snRNA), among others.

It has been determined that nucleic acids derivatized with oligomers can be delivered efficaciously. In some embodiments, nucleic acid does not alter the biological functions associated with the nucleic acid.

In some embodiments, derivatization imparts changes in the tertiary structure of the nucleic acid that increase the half-life or stability of the nucleic acid. In certain embodiments, nucleic acids increase the effective delivery of the nucleic acids to cells and tissues.

Accordingly, methods for the use of nucleic acids in methods of treating subjects and methods of affecting biological processes are provided. For example, a biological process can be affected by administering a functional nucleic acid to a cell or a subject, where the functional nucleic acid is derivatized nucleic acid.

In some forms of the method, the functional nucleic acid can be an aptamer, an antisense nucleic acid, an siRNA, an shRNA, or a crRNA. In some forms of the method, the functional nucleic acid can bind to or affect a molecule of interest. In some forms, the functional nucleic acid can be a substrate or cofactor for a nuclease. In some forms, the cofactor can be a substrate-guiding sequence (or guide), which directs a nuclease to cleave a substrate (an RNA or DNA). In some forms, effective delivery of derivatized nucleic acid compared to effective delivery of a corresponding nucleic acid that is not derivatized. In the case of functional nucleic acids, such as siRNA, shRNA, miRNA, crRNA, tracrRNA, and guide sequences, the derivatized forms can affect or alter the biological function of the function nucleic acid through more effective delivery.

A. Methods of Administration

The formulations can be administered subcutanteously, intramuscularly, or intradermally. In preferred embodiment, the formulation is injected subcutaneously.

In some embodiments, there is provided a method of treating a subject in need of such a treatment by administering to the subject a therapeutically effective amount of a therapeutic, prophylactic, or diagnostic agent, such as functional nucleic acid, derivative together with a pharmaceutically acceptable carrier and pharmaceutical acceptable additives.

In some embodiments, there is provided a use of a therapeutic, prophylactic, or diagnostic agent, such as functional nucleic acid, derivative for the manufacture of a medicament for treating a subject with the therapeutic, prophylactic, or diagnostic agent.

"Dosage unit form" as used herein refers to a physically discrete unit of conjugate appropriate for the patient to be treated. In one embodiment, the formulation is a therapeutic, prophylactic, or diagnostic agent, such as functional nucleic acid, formulation designed to deliver therapeutic, prophylactic, or diagnostic agent, to cells and tissues where it will be effective following injection in a patient.

B. Subjects to be Treated

The compositions and formulations including a responsive composition can be administered to a subject in need of delivery of a therapeutic, prophylactic, or diagnostic agent, such as functional nucleic acid. Generally, the subjects can be those that have a disease or condition, or that are suspected of having a disease or condition, the treating, diagnosis, prognosis, etc. of which the agent is designed to facilitate. For example, subjects having abnormal expression of a protein can be treated with a derivatized siRNA that targets the gene for that protein. The matching of therapeutic, prophylactic, or diagnostic agents, including functional nucleic acids, to diseases and conditions is generally known. Such knowledge can be applied to the use and delivery of the derivatized agents described herein.

The present invention will be further understood by reference to the following non-limiting examples.

EXAMPLES

Example 1. Oligomer Library Synthesis and Testing

This example describes a system for combinatorially generating oligomeric conjugates, attaching them to siRNA, and evaluating immunogenicity and delivery in vitro and in vivo. Using a defined set of thirteen synthetic monomers, a library of 2,197 trimeric conjugates can be made which possess unique delivery properties. This system is a high-yield and efficient oligomerization strategy that provides effective synthesis, purification, and characterization of synthetic conjugates (FIG. 1).

Figure 1C:
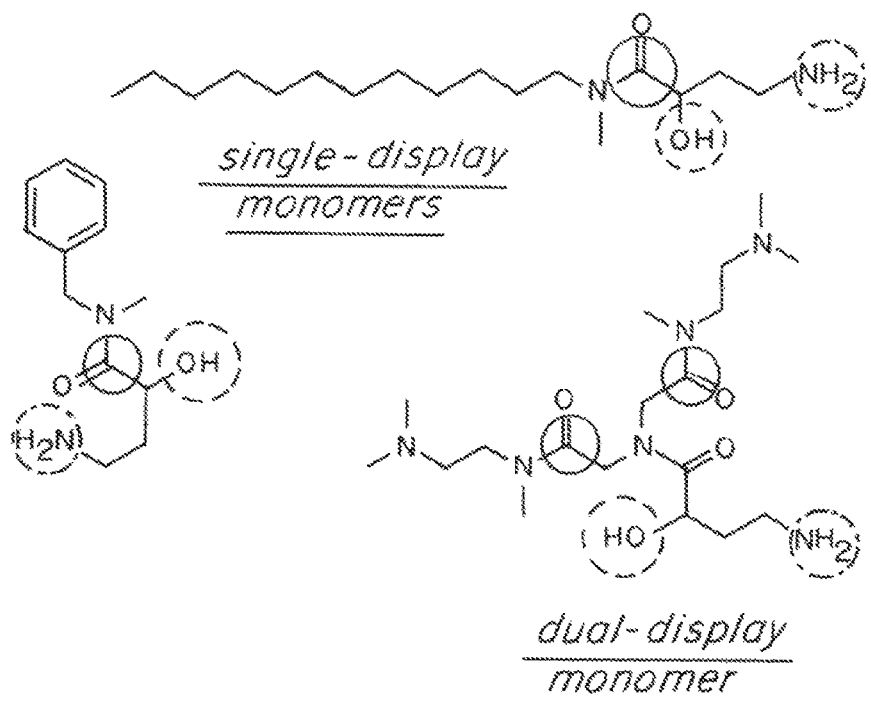
Figure 1B:
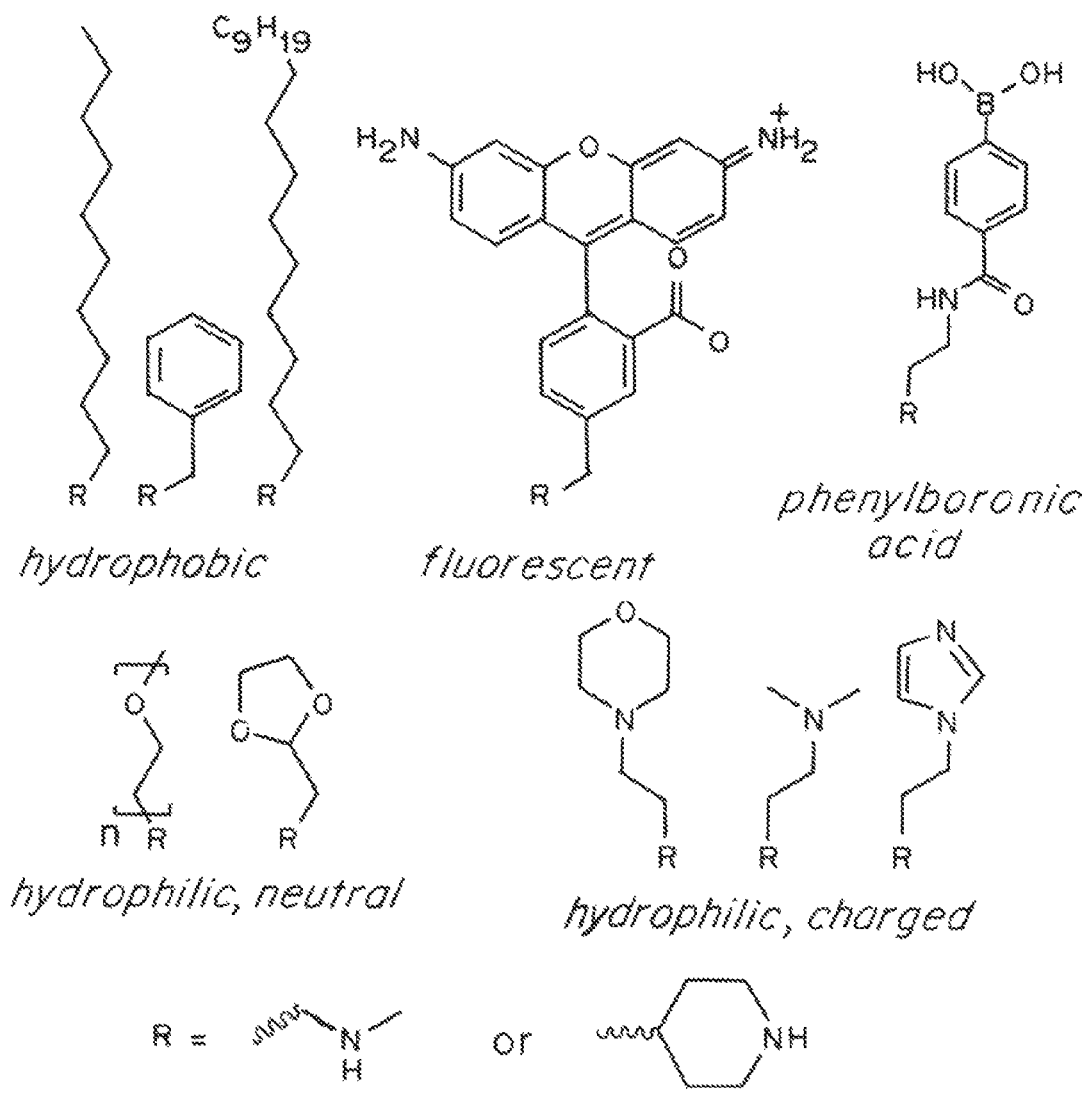
Figure 1D:
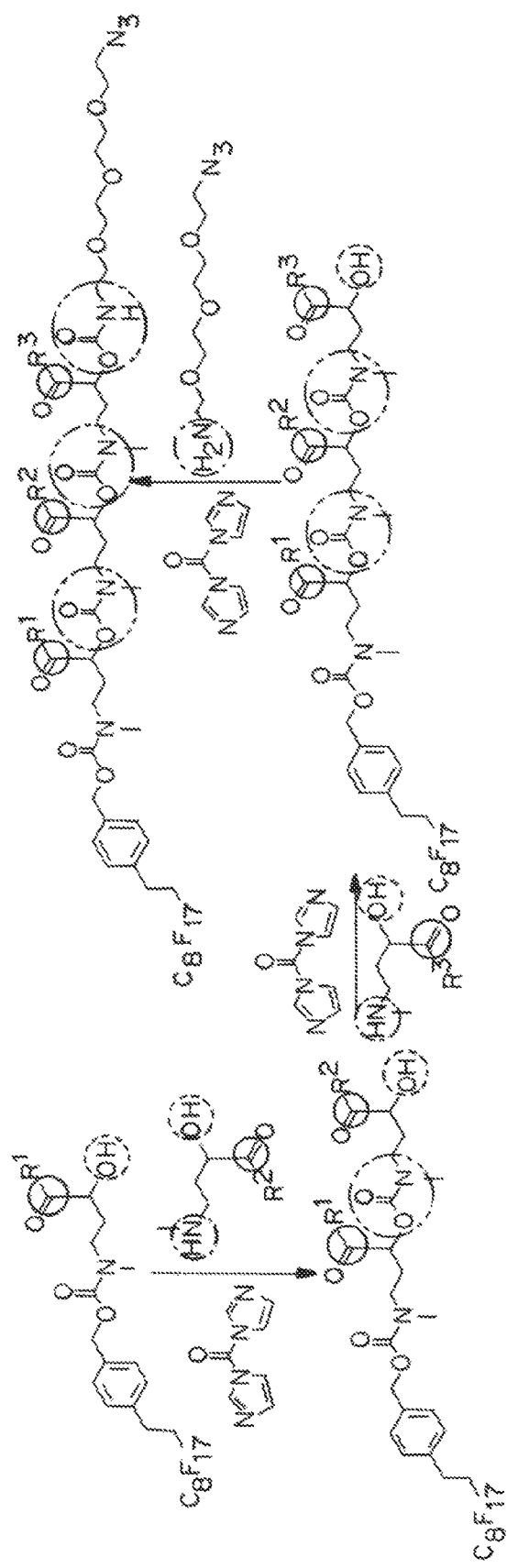

Three different chemical moieties are required on each monomer building block to ensure orthogonality between monomer functionalization and control over oligomerization. The presence of amine, alcohol, and carboxylic acid on each monomer building block allowed for attachment of delivery-biasing functionalities and oligomerization (FIGS. 1A-1C). Amidation of the carboxylic acid with delivery-biasing functionalities leaves free the alcohol and amine moieties on each monomer, which can be used for carbamate oligomerization (FIG. 1C). Carbamates are stable, non-degradable functionalities that can be synthesized using high-yielding reactions. Carbamate oligomerization using carbonyldiimidazole (CDI) is preferred because of its effectiveness (FIG. 1C). The reagent carbonyldiimidazole effectively coupled individual monomers in a controlled manner with near complete conversion as monitored by both LCMS and NMR analysis. A fluorous tag purification strategy was used, which provided isolated synthesized trimmers of 90% purity or better.

Based on nanoparticle formulations, it was discovered that certain functional groups are delivery-relevant (Table 1 and FIGS. 1A-1C). These chemical functional groups can be used to bias synthetic conjugates and ensure efficacious delivery. Acyl hydrocarbon chains have demonstrated utility in liposomal formulations and are credited with playing a major role in cellular internalization as well as endosomal membrane disruption [7, 14, 18, 21]. The inclusion of amine bases has been a cornerstone of a number of formulations for both DNA and siRNA delivery. The high pKa of most amine bases, such as tertiary and secondary amines, allows them to carry a positive charge at physiological pH, facilitating condensation with oligonucleotides, association with cellular membrane, and aiding endosomal escape [2, 7, 14, 18, 20, 21].

TABLE 1

Implicated delivery role of different functionalities.

| Functionality | Role in Delivery |
| --- | --- |
| hydrophobic, lipophilic | membrane association and disruption |
| amines | nucleic acid condensation, membrane association, endosomal escape |
| hydrophilic | systemic stability, cellular uptake |

It was realized from mechanistic studies that formulations with amines that have pKa's in the physiological range access different internalization pathways in vivo and have reduced toxicity than high pKa amines. Neutral and hydrophilic moieties such as PEG increase the systemic stability of nanoparticles and play a role in uptake [44]. Using these realizations as a framework, the system here functionalizes the monomers with thirteen nonpolar cyclic and acyclic hydrocarbon side chains, tertiary amines, cyclic amines with physiological pKa's, and both cyclic and acyclic neutral hydrophilic moieties. In addition, the inclusion of a fluorescent monomer can create conjugates that can be used as imaging agents of delivery.

Figure 1E:
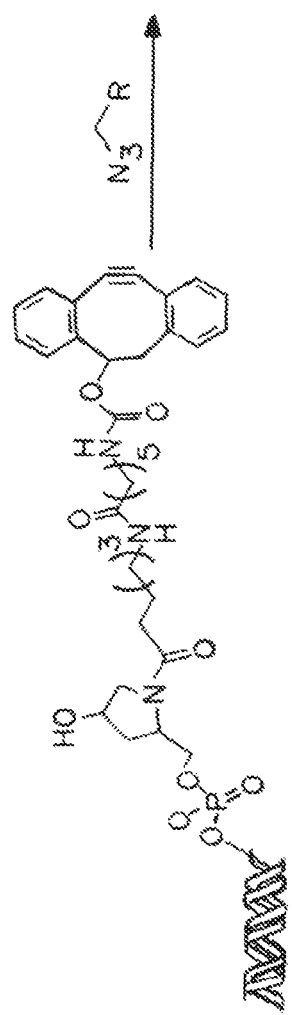
Figure 1E:
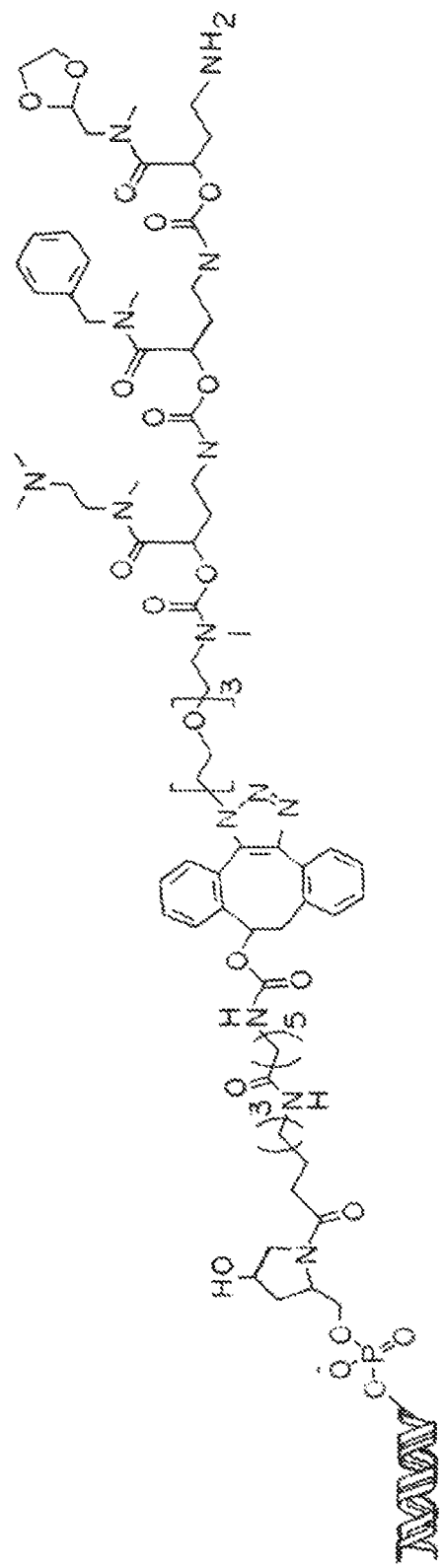

Previous studies identified the 3' end of the sense strand as an ideal location for the modification of siRNA without adversely affecting activity [11-13]. It was discovered that copper-free Huisgen cycloaddition, the coupling between cyclooctyne and azide to form stable triazine conjugation, is a high yielding and attractive method for oligomer-siRNA attachment (FIG. 1E). The alkyne-azide pair represents two chemical moieties that are inert to other chemistries making their implementation orthogonal to other reactions used for monomer functionalization and oligomerization. Amidation of siRNA bearing the 3' sense strand pyrrolidine linker with dibenzo-cyclooctyne will yield an alkyne-bearing siRNA that should easily react with azide-bearing conjugates. The only major drawback to this conjugation approach is the need to synthesize the dibenzo-cyclooctyne reagent. In a typical experiment, single-stranded dibenzo-cyclooctyne modified siRNA was reacted with azide-functionalized oligomer at two different ratios of oligomer to siRNA under RNAse-free conditions with acetonitrile as a co-solvent. The reaction mixtures were then characterized for coupling by using a gel-shift mobility assay. Successful conjugation was evident by the lowered mobility of the siRNA in the gel.

The ability of synthetic oligomers to impact delivery without adversely affecting the cellular mechanisms behind siRNA processing is dependent on conjugate size and the representation of the delivery-biasing elements. For this reason, conjugates preferably will have molecular weights much larger than small molecules but slightly smaller than the siRNA molecules themselves. To make full use of this mass range and maximize the representation of the delivery-facilitating functionalities, trimeric conjugates that contain monomers with single-modified and dual-modified sidechains are preferred (FIGS. 1A-1C).

Figure 2:
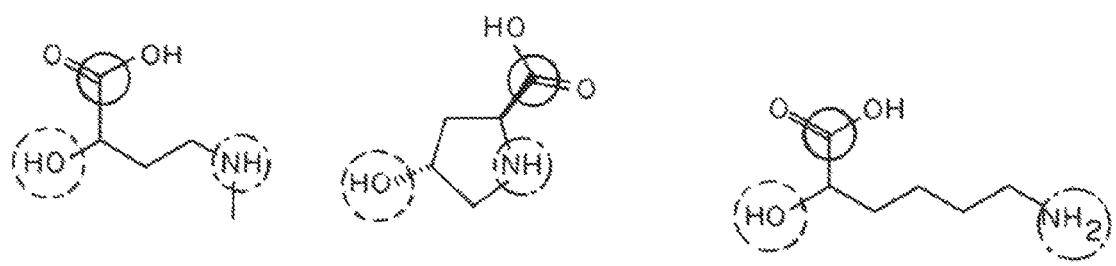
FIG. 2 is a diagram of alternative monomer backbone frameworks.

A variety of monomer backbones (also referred to monomer building blocks) can be used to provide for more or fewer side chains and to account for reactivity differences between monomers. Some examples of alternatives are shown in FIG. 2.

The oligomer conjugates can be evaluated and optimized for efficacious siRNA delivery. For example, conjugates that display greater than 50% protein knockdown in vitro (using mouse cancer cell lines) can be tested in mice for biodistribution and endogenous gene silencing in the liver and lung. Immunogenicity can be determined by monitoring mouse cytokine levels. Oligomers displaying combinations of delivery-based functionalities will exhibit increased siRNA delivery in vitro and in vivo. Oligomer conjugates of most interest will exhibit low immunogenicity and greater than 90% protein knockdown in vivo when administered at 1 mg/kg body weight. The mechanism of oligomer-mediated siRNA delivery can be assessed in appropriate cells, such as primary mouse hepatocyte and primary mouse lung epithelial cells, by testing one or more of four different internalizations routes: clathrin-mediated endocytosis, caveolae-mediated endocytosis, charge-based cell penetration, and serum protein-mediated uptake. The oligomer conjugates can be make use of more than one delivery route, which can aid in improved and efficient delivery.

The oligomer conjugates can also be evaluated for numerous properties, such as pKa and hydrophobicity. Correlation of these properties to the effectiveness of the oligomer conjugates can be used to guide optimization of the oligomer conjugates. For example, the properties and oligomer conjugate activity can be subjected to principal component analysis (PCA) to illuminate design principles [15, 16].

The oligomer conjugates represent new means of effectively delivering siRNA to cells and tissues as well as new tools for siRNA research and development of siRNA-based therapies.

Therapeutic intervention with small-interfering RNA (siRNA) is a promising strategy for the silencing of disease-associated genes [1, 2]. Exogenous siRNA sequences can utilize the cellular mechanism of RNA interference (RNAi) to catalyze the destruction of complementary protein-encoding RNA sequences, resulting in sequence-specific gene silencing [3-6]. The prevalence of disease targets considered "undruggable" using small molecules or protein-based therapies underscores the importance of pursuing siRNA-based approaches to improve clinical outcomes for a wide range of diseases [1].

A major obstacle to implementation of siRNA therapy is systemic delivery of the oligonucleotide in vivo [7]. Polymeric or liposomal approaches have progressed towards resolving this challenge but require excess delivery material relative to siRNA, leading to issues associated with toxicity and practicality [7-14]. An alternative approach involves one-to-one modification of siRNA with chemical or biological entities that can facilitate delivery. This approach overcomes the use of excess delivery material, making it an attractive strategy to facilitate cellular delivery while minimizing unfavorable biological responses [8-10]. Conjugation of biological motifs to siRNA has achieved mixed results with limitations to clinical implementation, while small chemical entities have to date proven inefficacious [8,11,12]. Cholesterol-conjugates siRNA is the most efficacious small molecule formulation, but this approach requires doses that are intractable for therapeutic use [11-13]. Cell-penetrating peptides are efficacious in assisting delivery of payloads, but are considerably immunogenic due to the use of non-human peptides sequences [8]. To date, there are no reported investigations whether a fully synthetic, peptide-mimetic conjugate system can capture the delivery potential of large polymeric molecules while displaying low immunogenicity at therapeutically relevant doses.

Previous approaches for conjugate-mediated siRNA delivery have relied upon existing chemical or biological motifs to facilitate cellular internalization. Nanoparticle formulations are an efficacious siRNA delivery agents, but there has been no investigation into whether the chemical functionalities that facilitate efficient delivery can be translated into smaller distinct chemical entities that can serve as covalently attached conjugates.

The system described here uses these delivery-biasing chemical moieties in a synthetic oligomeric approach to develop siRNA delivery conjugates. To accommodate the numerous chemical functionalities that have been implicated in successful delivery, a defined set of delivery-biased building blocks were devised to serve as monomers, with the monomers used to build trimeric oligomers. The combinatorial pairing of delivery-relevant functionalities can generate thousands of unique oligomers with promising delivery potential.

This approach makes generation of efficient delivery of siRNA easier and allows analysis of the structure-function relationships of the oligomers to elucidate the most salient molecular properties for efficacious delivery. This approach is the first time multiple delivery-relevant functionalities have been brought together in an oligomeric framework to identify optimal delivery agents while illuminating properties that govern delivery. Beyond their use for treatment of patients, the development of synthetic delivery conjugates are also useful tools for siRNA research and to provide understanding of chemical properties required to overcome cellular barriers.

REFERENCES

1. Dorsett, Y.: Tuschl, T., siRNAs: applications in functional genomics and potential as therapeutics. *Nat Rev Drug Discov* 2004, 3 (4), 3-18-29.
2. Davis, M. E.; Zuckerman, J. E.; Choi, C. H.; Seligson D.; Tolcher, A.; Alabi, C. A.; Yen, Y.; Heidel, J. D.; Ribas, A., Evidence of RNAi in humans from systemically administered siRNA via targeted nanoparticles. *Nature* 464 (7291), 1067-70,
3. Caplen, N. J.; Parrish, S.; Imani, F.; Fire, A.; Morgan, R. A., Specific inhibition of gene expression by small double-stranded RNAs in invertebrate and vertebrate systems. *Pro Natl Acad Sci USA* 2001, 98 (17), 9742-7.
4. Elbashir, S. M.; Harborth, J.; Lendeckel, W.; Yalcin, A.; Weber, K.; Tuschl, T., Duplexes of 21-nucleotide RNAs mediate RNA interference in cultured mammalian cells. *Nature* 2001, 411 (6836), 494-8.
5. Hannon, G. J.; Rossi, J. J.; Unlocking the potential of the human genome with RNA interference. *Nature* 2004, 431 (7006), 371-8.
6. McManus, M. T.; Sharp, P. A., Gene silencing in mammals by small interfering RNAs. *Nat Rev Genet* 2002, 3 (10), 737-47.
7. Whitehead, K. A.; Langer, R.; Anderson, D. G., Knocking down barriers: advances in siRNA delivery. *Nat Rev Drug Discov* 2009, 8 (2), 129-38.
8. Jeong, J. H.; Mok, H.; Oh, Y. K.; Park, T. G., siRNA conjugate delivery systems. *Bioconjug Chem* 2009, 20 (1), 5-14.
9. Stanton, M. G.; Colletti, S. L., Medicinal Chemistry of siRNA Delivery. *J Med Chem*.

10. Vaishnaw, A. K.; Gollob, J.; Gamba-Vitalo, C.; Hutabarat, R.; Sah, D.; Meyers, R.; de Fougerolles, T.; Maraganore, J., A status report on RNAi therapeutics. *Silence* 1 (I), 14.
11. Lorenz, C.; Hadwiger, P.; John, M.; Vornlocher, H. P.; Unverzagt, c., Steroid and lipid conjugates of siRNAs to enhance cellular uptake and gene silencing in liver cells. *Bioorg Med Chem Lett* 2004, 14 (19), 4975-7.
12. Soutschek, J.; Akinc, A.; Bramlage, B.; Charisse, K.; Constien, R.; Donoghue, M.; Elbashir, S.; Geick, A.; Hadwiger, P.; Harborth, J.; John, M.; Kesavan, V.; Lavine, G.; Pandey, R. K.; Racie, T.; Rajeev, K. G.; Rohl, I.; Toudjarska, I.; Wang, G.; Wuschko, S.; Bumcrot, D.; Koteliansky, V.; Limmer, S.; Manoharan, M.; Vornlocher, H. P., Therapeutic silencing of an endogenous gene by systemic administration of modified siRNAs. *Nature* 2004, 432 (7014), 173-8.
13. Wolfrum, C.; Shi, S.; Jayaprakash, K. N.; Jayaraman, M.; Wang, G.; Pandey, R. K.; Rajeev, K. G.; Nakayama, T.; Charrise, K.; Ndungo, E, M.; Zimmermann, T.; Koteliansky, V.; Manoharan, M.; Stoffel, M., Mechanisms and optimization of in vivo delivery of lipophilic siRNAs. *Nat Biotechnol* 2007, 25 (10), 1149-57.
14. Schroeder, A.; Levins, C. G.; Cortez, C.; Langer, R.; Anderson. D. G., Lipid-based nanotherapeutics for siRNA delivery. *J Intern Med* 267 (I), 9-21.
15. Leonard, J. T.; Roy, K., QSAR by LFER model of HIV protease inhibitor mannitol derivatives using FA-MLR, PCRA, and PLS techniques. *Bioorg Med Chem* 2006, 14 (4), 1039-46.
16. XU, Q.; Ni, S.; Wu, F.; Liu, F.; Ye, X.; Mougin, B.; Meng, Xc; Du, X., Investigation of Variation in Gene Expression Profiling of Human Blood by Extended Principle Component Analysis. *PLoS One* 6 (10), e26905.
17. Akinc, A.; Querbes, W.; De, S.; Qin, J.; Frank-Kamenetsky, M.; Jayaprakash, K. N.; Jayaraman, M.; Rajeev, K. G.; Cantley, W. L.; Dorkin, J. R.; Butler, J. S.; Qin, L.; Raeie, T.; Sprague, A.; Fava, E.; Zeigerer, A.; Hope, M. J.; Zenal, M.; Sah, D. W.; Fitzgerald, K.; Tracy, M. A; Manoharan, M.; Koteliansky, V.; Fougerolles, A.; Maier, M. A., Targeted delivery of RNAi therapeutics with endogenous and exogenous ligand-based mechanisms. *Mol Ther* 18 (7), 1357-64.
18. Akinc, A.; Zumbuehl, A; Goldberg, M.; Leshchiner, E. S.; Busini, V.; Hossain, N.; Bacallado, S. A.; Nguyen, D. N.; Fuller, J.; Alvarez, R.; Borodovsky, A; Borland, T.; Constien. R.; de Fougerolles. A.; Dorkin, J. R.; Narayanannair Jayaprakash, K.; Jayaraman, M.; John, M.; Koteliansky, V.; Manoharan, M.; Nechev, L.; Qin, J.; Racie, T.; Raitcheva, D.; Rajeev, K. G.; Sah, D. W.; Soutschek, J.; Toudjarska, I.; Vomlocher, H. P.; Zimmermann, T. S.; Langer, R.; Anderson, D. G., A combinatorial library of lipid-like materials for delivery of RNAi therapeutics. *Nat Biotechnol* 2008, 26 (5), 561-9.
19. Love, K. T.; Mahon, K. P.; Levins, C. G.; Whitehead, K. A.; Querbes, W.; Dorkin, J. R.; Qin, J.; Cantley, W.; Qin, L. L.; Racie, T.; Frank-Kamenetsky, M.; Yip, K. N.; Alvarez, R.; Sah, D. W.; de Fougerolles, A.; Fitzgerald, K.; Koteliansky, V.; Akinc, A.; Langer, R.; Anderson, D. G., Lipid-like materials for low-dose, in vivo gene silencing. *Proc Natl Acad Sci USA* 107 (5), 1864-9.
20. Mahon, K. P.; Love, K. T.; Whitehead, K. A.; Qin J.; Akinc, A.; Leshchiner, E.; Leshchiner, I.; Langer, R.; Anderson, D. G., Combinatorial approach to determine functional group effects on lipidoid-mediated siRNA delivery. *Bioconjug Chem* 21 (8), 1448-54.
21. Semple, S. C.; Akinc, A.; Chen, J.; Sandhu, A. P.; Mui, B. I.; Cho, C. K.; Sah, D. W.; Stebbing, D.; Crosley, E. J.; Yaworski, E.; Hafez, I. M.; Dorkin, J. R.; Qin, J.; Lam, K.; Rajeev, K. G.; Wong, K. F.; Jeffs, L. B.; Nechev, L.; Eisenhardt, M. L.; Jayararnan, M.; Kazem, M.; Maier, M. A.; Srinivasulu, M.; Weinstein, M. J.; Chen, Q.; Alvarez, R.; Barros, S. A.; De, S.; Klimuk, S. K.; Borland, T.; Kosovrasti, V.; Cantley, W. L.; Tam, Y. K.; Manoharan, M.; Ciufolini, M. A.; Tracy, M. A.; de Fougerolles, A.; MacLachlan, I.; Cullis, P. R; Madden, T. D.; Hope, M. J., Rational design of cationic lipids for siRNA delivery. *Nat Biotechnol* 28 (2), 172-6.
22. Rozema, D. B.; Lewis, D. L.; Wakefield, D. H.; Wong, S. c.; Klein, J. J.; Roesch, P. L.; Bertin, S. L.; Reppen, T. W.; Chu, Q.; Blokhin, A. V.; Hagstrom, J. E.; Wolff, J. A., Dynamic PolyConjugates for targeted in vivo delivery of siRNA to hepatocytes. *Proc Nat. Acad Sci USA* 2007, 104 (32), 12982-7.
23. Astriab-Fisher, A.; Sergueev, D.; Fisher, M.; Shaw, B. R.; Juliano, R. L., Conjugates of antisense oligonucleotides with the Tat and antennapedia cell-penetrating peptides: effects on cellular uptake; binding to target sequences, and biologic actions. *Pharm Res* 2002, 19 (6), 744-54.
24. Astriab-Fisher, A.; Sergueev, D. S.; Fisher, M.; Shaw, B. R; Juliano, R. 1., Antisense inhibition of P-glycoprotein expression using peptide-oligonucleotide conjugates. *Biochem Pharmacol* 2000, 60 (I), 83-90.
25. Chiu, Y. L.; Ali, A.; Chu, C. Y.; Cao, H.; Rana, T. M., Visualizing a correlation between siRNA localization, cellular uptake, and RNAi in living cells. *Chem Biol* 2004, 11 (8), 1165-75.
26. Davidson, T. J.; Harel, S.; Arboleda, V. A.; Prunell, G. F.; Shelanski, M. L.; Greene, L. A.; Troy, C. M., Highly efficient small interfering RNA delivery to primary mammalian neurons induces MicroRNA-like effects before mRNA degradation. *J Neurosci* 2004, 24 (45), 10040-6.
27. Kim, D. H.; Behlke, M. A.; Rose, S. D.; Chang, M. S.; Choi, S.; Rossi, J. J., Synthetic dsRNA Dicer substrates enhance RNAi potency and efficacy. *Nat Biotechnol* 2005, 23 (2), 222-6.
28. Lindgren, M.; Hallbrink, M.; Prochiantz, A.; Langel, U., Cell-penetrating peptides. *Trends Pharmacol Sci* 2000, 21 (3), 99-103.
29. Moschos, S. A.; Jones, S. W.; Perry, M. M.; Williams, A. E.; Etjefalt, J. S.; Turner, J. J.; Barnes, P. J.; Sproat, B. S.; Gait, M. J.; Lindsay, M. A., Lung delivery studies using siRNA conjugated to TAT(48-60) and penetratin reveal peptide induced reduction in gene expression and induction of innate immunity. *Bioconjug Chem* 2007, 18 (5), 1450-9.
30. Muratovska, A.; Eccles, M. R., Conjugate for efficient delivery of short interfering RNA (siRNA) into mammalian cells. *FEBS Lett* 2004, 558 (1-3), 63-8.
31. Pooga, M.; Hallbrink, M.; Zorko, M.; Langel, U., Cell penetration by transportan. *FASEB J* 1998, 12 (I), 67-77.
32. Prochiantz, A., [Messenger proteins] *J Soc Biol* 2000, 194 (3-4), 119-23.
33. Tripathi, S.; Cbaubey, B.; Ganguly, S.; Harris, D.; Casale, R. A.; Pandey, V. N., Anti-HIV-I activity of anti-TAR polyamide nucleic acid conjugated with various membrane transducing peptides. *Nucleic Acids Res* 2005, 33 (13), 4345-56.
34. Turner, J. J.; Arzumanov, A. A.; Gait, M. J., Synthesis, cellular uptake and HIV-I Tat-dependent trans-activation inhibition activity of oligonucleotide analogues disulphide-conjugated to cell-penetrating peptides. *Nucleic Acids Res* 2005, 33 (I), 27-42.

35. Turner, J. J.; Ivanova, G. D.; Verbeure, B.; Williams, D.; Arzumanov, A. A.; Abes, S.; Lebleu, B.; Gait, M. J., Cell-penetrating peptide conjugates of peptide nucleic acids (PNA) as inhibitors of HIV-I Tat-dependent transactivation in cells. *Nucleic Acids Res* 2005, 33 (21), 6837-49.

36. Vives, E.; Brodin, P.; Lebleu, B., A truncated HIV-I Tat protein basic domain rapidly translocates through the plasma membrane and accumulates in the cell nucleus. *J Biol Chem* 1997, 272 (25), 16010-7.

37. Cesarone, G.; Edupuganti, O. P.; Chen, C. P.; Wickstrom, E., Insulin receptor substrate 1 knockdown in human MCF7 ER+ breast cancer cells by nuclease-resistant IRS 1 siRNA conjugated to a disulfide-bridged D-peptide analogue of insulin-like growth factor I. *Bioconjug Chem* 2007, 18 (6), 1831-40.

38. Ikeda, Y.; Taira, K., Ligand-targeted delivery of therapeutic siRNA. *Pharm Res* 2006, 23 (8), 1631-40.

39. Wu, G.; Yang, W.; Barth, R. F.; Kawabata, S.; Swindall, M.; Bandyopadhyaya, A. K.; Tjarks, W.; Khorsandi, B.; Blue, T. E.; Ferketich, A. K.; Yang, M.; Christoforidis, G. A.; Sferra, T. J.; Binns, P. J.; Riley, K. J.; Ciesielski, M. J.; Fenstennaker, R. A., Molecular targeting and treatment of an epidermal growth factor receptor-positive glioma using boronated cetuximab. *Clin Cancer Res* 2007, 13 (4), 1260-8.

40. Chu, T. C.; Twu, K. Y; Ellington, A. D.; Levy, M., Aptamer mediated siRNA delivery. *Nucleic Acids Res* 2006, 34 (10), e73.

41. Hicke, B. J.; Stephens, A. W., Escort aptamers: a delivery service for diagnosis and therapy. *J Clin Invest* 2000, 106 (8), 923-8.

42. Xia, C. F.; Zhang, Y.; Boado, R. J.; Pardridge, W. M., Intravenous siRNA of brain cancer with receptor targeting and avidin-biotin technology. *Pharm Res* 2007, 24 (12), 2309-16.

43. Zhang, Y.; Zhang, Y. F.; Bryant, J.; Charles, A.; Boado, R. J.; Pardridge, W. M., Intravenous RNA interference gene therapy targeting the human epidermal growth factor receptor prolongs survival in intracranial brain cancer. *Clin Cancer Res* 2004, 10 (11), 3667-77.

44. Harris, J. M.; Martin, N. E.; Modi, M., Pegylation: a novel process for modifying pharmacokinetics. *Clin Pharmacokinet* 2001, 40 (7), 539-51.

45. Yamada, T.; Peng, C. G.; Matsuda, S.; Addepalli, H.; Jayaprakash, K. N.; Alam, M. R.: Mills, K.; Maier, M. A.; Charisse, K.; Sekine, M.; Manoharan, M.; Rajeev, K. G., Versatile site-specific conjugation of small molecules to siRNA using click chemistry. *J Org Chem* 76 (5), 1198-211.

46. Cramer, J. A.; Pugh, M. J., The influence of insulin use on glycemic control: How well do adults follow prescriptions for insulin? *Diabetes Care* 2005, 28 (Copyright (C) 2012 U.S. National Library of Medicine.), 78-83.

47. Browning, J. D.; Szczepaniak, L. S.; Dobbins, R.; Nuremberg, P.; Horton, J. D.; Cohen, J. C.; Grundy. S. M.; Hobbs, H. H., Prevalence of hepatic steatosis in an urban population in the United States: Impact of ethnicity. *Hepatology* 2004, 40 (6), 1387-1395.

48. Berman, M., Insulin kinetics, models, and delivery schedules. *Diabetes Care* 1980, 3 (Copyright (C) 2012 American Chemical Society (ACS). All Rights Reserved.), 266-9.

49. Esposito, K.; Giugliano, D., Current insulin analogues in the treatment of diabetes: emphasis on type 2 diabetes. *Expert Opin. Biol. Ther.* 2012, 12 (Copyright (C) 2012 American Chemical Society (ACS). All Rights Reserved.), 209-221.

50. Siddiqui, N. I., Insulin analogues: new dimension of management of diabetes mellitus. *Mymensingh Med J* 2007, 16 (Copyright (C) 2012 U.S. National Library of Medicine.), 117-21.

51. Helms, K. L.; Kelley, K. W.; Insulin glulisine: an evaluation of its pharmacodynamic properties and clinical application. *Ann. Pharmacother.* 2009, 43 (Copyright (C) 2012 American Chemical Society (ACS). All Rights Reserved.), 658-668.

52. Gerich, J. E., Novel insulins: expanding options in diabetes management. *Am. J. Med.* 2002, 113 (Copyright (C) 2012 American Chemical Society (ACS). All Rights Reserved.), 308-316.

53. Hinds, K.; Koh, J. J.; Joss, L.; Liu, F.; Baudys, M.; Kim, S. W., Synthesis and Characterization of Poly(ethylene glycol)-Insulin Conjugates. *Bioconjugate Chem.* 2000, 11 (Copyright (C) 2012 American Chemical Society (ACS). All Rights Reserved.), 195-201.

54. Shechter, Y.; Mironchik, M.; Rubinraut, S.; Tsubery, H.; Sasson, K.; Marcus, Y.; Fridkin, M., Reversible pegylation of insulin facilitates its prolonged action in vivo. *Eur. J. Pharm. Biopharm.* 2008, 70 (Copyright (C) 2012 American Chemical Society (ACS). All Rights Reserved.), 19-28.

55. Szypowska, A.; Golicki, D.; Groele, L.; Pankowska, E., Long-acting insulin analogue detemir compared with NPH Insulin in type 1 diabetes. A systematic review and meta-analysis. *Pol. Arch. Med. Wewn,* 2011, 121 (Copyright (C) 2012 American Chemical Society (ACS). All Rights Reserved.), 237-246.

56. Lee, S.; Kim, K.; Xumar, T. S.; Lee, J.; Kim, S. K.; Lee, D. Y.; Lee, Y.-k.; Byun, Y., Synthesis and biological properties of insulin-deoxycholic acid chemical conjugates. *Bioconjugate Chem.* 2005, 16 (Copyright (C) 2012 American Chemical Society (ACS). All Rights Reserved.), 615-620.

57. Shechter, Y.; Mironchik, M.; Rubinraut, S.; Saul, A.; Tsubery, H.; Fridkin, M., Albumin-insulin conjugate releasing insulin slowly under physiological conditions: a new concept for long-acting insulin. *Bioconjugate Chem.* 2005, 16 (Copyright (C) 2012 American Chemical Society (ACS). All Rights Reserved.), 913-920.

58. Baudys, M.; Letourneur, D.; Liu, F.; Mix, D.; Jozefonvicz, J.; Kim, S. W., Extending Insulin Action in Vivo by Conjugation to Carboxymethyl Dextran. *Bioconjugate Chem.* 1998, 9 (Copyright (C) 2012 American Chemical Society (ACS). All Rights Reserved.), 176-183.

59. Gerich, J. E., Insulin glargine: long-acting basal insulin analog for improved metabolic control. *Curr. Med. Res. Opin.* 2004, 20 (Copyright (C) 2012 American Chemical Society (ACS). All Rights Reserved.), 31-37.

60. Phillips, N. B.; Wan, Z.-I.; Whittaker, L.; Hu, S.-Q.; Huang, K.; Hua, Q.-x.; Whittaker, J.; Ismail-Beigi, F.; Weiss, M. A., Supramolecular Protein Engineering: Design of Zinc-stapled Insulin Hexamers as a Long Acting Depot. *J. Bioi. Chem.* 2010, 285 (Copyright (C) 2012 American Chemical Society (ACS). All Rights Reserved.), 11755-11759.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A derivatized functional nucleic acid comprising the functional nucleic acid conjugated to an oligomer of 2 to 5 monomers,
wherein each monomer of the oligomer is —CO—O—$R_3$—, wherein $R_3$ is:
—$CR_4$—$(CH_2)_m$—NH— or pyrrolidine substituted with $R_4$, wherein m is an integer from 0 to 25,
wherein $R_4$ is —CO—NH—$R_5$ or —CO—NH—C(CH—CO—NH—$R_5$)$_2$,
wherein each $R_5$ is independently selected from the group consisting of phenylboronic acid groups, hydrophobic groups, hydrophilic neutral groups, hydrophilic charged groups, diol groups, fluorescent groups, and combinations thereof, and
wherein at least one $R_5$ is a hydrophilic charged group.

2. The derivatized functional nucleic acid of claim 1, wherein the hydrophobic groups are independently nonpolar cyclic hydrocarbon groups, and nonpolar acyclic hydrocarbon groups,
the hydrophilic charged groups are independently tertiary amine groups, and cyclic amine groups, and
the hydrophilic neutral groups are independently cyclic neutral hydrophilic groups, and acyclic neutral hydrophilic groups.

3. The derivatized functional nucleic acid of claim 1, wherein each $R_5$ is independently a nonpolar cyclic hydrocarbon group, a nonpolar acyclic hydrocarbon group, a tertiary amine group, a cyclic amine group, a cyclic neutral hydrophilic group, or a acyclic neutral hydrophilic group.

4. The derivatized functional nucleic acid of claim 1, wherein each $R_5$ is independently:
(a) a phenylboronic acid group,
(b) $C_{8-18}$ alkyl,
(c) —$CH_2$-phenyl,
(d) —$(CH_2$—$CH_2$—O$)_p$—H or —$(CH_2$—$CH_2$—O$)_p$—$CH_3$, wherein p is an integer from 1-500,
(e) —$CH_2$-dioxane,
(f) —$CH_2$—$CH_2$-oxazane,
(g) —$CH_2$—$CH_2$—$N(CH_2$—$CH_3)_2$,
(h) —$CH_2$—$CH_2$-pyrazole,
(i) a fluorescent group,
(j) -piperidine-phenyl,
(k) -piperidine-oxazane,
(l) -piperidine-$CH_2$—$CH_2$—$N(CH_2$—$CH_3)_2$,
(m) -piperidine-$CH_2$—$CH_2$-pyrazole,
(n) -dimethylaminobenzyl, or
(o) -pyridine.

5. The derivatized functional nucleic acid of claim 1, wherein the functional nucleic acid is an siRNA, an aptamer, an antisense nucleic acid, an shRNA, a ribozyme, a triplex forming molecule, CRISPR (Clustered Regularly Interspaced Short Palindromic Repeats) RNA (crRNA), or an external guide sequence.

6. A method of treating a subject comprising administering to the subject the derivatized functional nucleic acid of claim 1, wherein the derivatized functional nucleic acid affects a biological process of the subject.

7. A method of affecting a biological process, the method comprising administering the derivatized functional nucleic acid of claim 1 to a cell or a subject.

8. A method of making a derivatized functional nucleic acid according to claim 1, the method comprising:
(i) reacting a first monomer with a second monomer, wherein the monomers each comprise an amine moiety, an alcohol moiety, and a modified sidechain, wherein the alcohol moiety of the first monomer and the amine moiety of the second monomer are linked via a carbamate reaction to produce a dimer;
(ii) reacting the dimer with a third monomer, wherein the third monomer comprises an amine moiety, an alcohol moiety, and a modified sidechain, wherein the alcohol moiety of the dimer and the amine moiety of the third monomer are linked via a carbamate reaction to produce a trimer;
(iii) reacting the trimer with an azide-containing group, wherein the azide-containing group comprises an azide moiety and an alcohol moiety, wherein the alcohol moiety of the azide-containing moiety and the amine moiety of the first monomer are linked via a carbamate reaction to produce an azide-trimer;
(iv) reacting the azide-trimer with an alkyne-derivatized functional nucleic acid, wherein the azide moiety and the alkyne moiety of the alkyne-derivatized functional nucleic acid are linked to produce the derivatized functional nucleic acid,
wherein each monomer of the oligomer is —CO—O—$R_3$—, wherein $R_3$ is:
—$CR_4$—$(CH_2)_m$—NH— or pyrrolidine substituted with $R_4$, wherein m is an integer from 0 to 25, wherein $R_4$ is —CO—NH—$R_5$ or —CO—NH—C(CH—CO—NH—$R_5$)$_2$, wherein each $R_5$ is independently selected from the group consisting of phenylboronic acid groups, hydrophobic groups, hydrophilic neutral groups, hydrophilic charged groups, diol groups, fluorescent groups, and combinations thereof, and
wherein at least one $R_5$ is a hydrophilic charged group.

9. The method of claim 8, wherein step (i) is performed a plurality of times using a different first monomer, a different second monomer, or different first and second monomers.

10. The method of claim 8, wherein step (ii) is performed a plurality of times using a different dimer, a different third monomer, or a different dimer and a different third monomer.

11. The method of claim 8, wherein the monomers are prepared by reacting a monomer backbone with a sidechain modifying group, wherein the monomer backbone comprises a carboxylic acid moiety, an amine moiety, and an alcohol moiety, wherein the sidechain modifying group comprises an amine group, wherein the sidechain modifying group amidates the carboxylic acid moiety via the amine group.

12. The method of claim 8, wherein the sidechain modifying groups are independently a hydrophobic group, a hydrophilic group, a neutral group, an amine-containing group, a charged group, or a fluorescent group.

13. The method of claim 8, wherein the sidechain modifying groups are independently a nonpolar cyclic hydrocarbon group, a nonpolar acyclic hydrocarbon group, a tertiary amine group, a cyclic amine group, a cyclic neutral hydrophilic group, or an acyclic neutral hydrophilic group.

14. The method of claim 8, wherein each $R_5$ is independently a nonpolar cyclic hydrocarbon group, a nonpolar acyclic hydrocarbon group, a tertiary amine group, a cyclic amine group, a cyclic neutral hydrophilic group, or a acyclic neutral hydrophilic group.

15. The method of claim 8, wherein each $R_5$ is independently:
(a) a phenylboronic acid group,
(b) $C_{8-18}$ alkyl,
(c) —$CH_2$-phenyl,
(d) —$(CH_2$—$CH_2$—$O)_p$—H or —$(CH_2$—$CH_2$—$O)_p$—$CH_3$, wherein p is an integer from 1-500,
(e) —$CH_2$-dioxane,
(f) —$CH_2$—$CH_2$-oxazane,
(g) —$CH_2$—$CH_2$—$N(CH_2$—$CH_3)_2$,
(h) —$CH_2$—$CH_2$-pyrazole,
(i) a fluorescent group,
(j) -piperidine-phenyl,
(k) -piperidine-oxazane,
(l) -piperidine-$CH_2$—$CH_2$—$N(CH_2$—$CH_3)_2$,
(m) -piperidine-$CH_2$—$CH_2$-pyrazole,
(n) -dimethylaminobenzyl, or
(o) -pyridine.

16. The method of claim 8, wherein the functional nucleic acid is an siRNA, an aptamer, an antisense nucleic acid, an shRNA, a ribozyme, a triplex forming molecule, CRISPR (Clustered Regularly Interspaced Short Palindromic Repeats) RNA (crRNA), or an external guide sequence.

17. The method of claim 8 further comprising:
(v) testing the derivatized functional nucleic acid for function, stability, immunogenicity, or a combination, wherein function of the derivatized functional nucleic acid above a threshold, stability of the derivatized functional nucleic acid above a threshold, immunogenicity below a threshold, or a combination, identifies the derivatized functional nucleic acid as useful for delivery of the functional nucleic acid.

18. A derivatized functional nucleic acid made by the method of claim 8.

* * * * *